US012672827B2

(12) United States Patent
Leo et al.

(10) Patent No.:     US 12,672,827 B2
(45) Date of Patent:     *Jul. 7, 2026

(54) COMPACT FORCE SENSOR FOR CATHETERS

(71) Applicant: St. Jude Medical International Holding S.À R.L., Luxembourg (LU)

(72) Inventors: Giovanni Leo, Cologny (CH); Nicolas Aeby, Geneva (CH); Stuart J. Olstad, Plymouth, MN (US); Axel Bertholds, Verscio (CH); Pere Llosas, Minusio (CH)

(73) Assignee: St. Jude Medical International Holding S.À R.L., Luxembourg (LU)

( * ) Notice:     Subject to any disclaimer, the term of this patent is extended or adjusted under 35 U.S.C. 154(b) by 699 days.

This patent is subject to a terminal disclaimer.

(21) Appl. No.: 18/145,737

(22) Filed:     Dec. 22, 2022

(65)         Prior Publication Data

US 2023/0200736 A1     Jun. 29, 2023

Related U.S. Application Data

(60) Continuation of application No. 16/736,570, filed on Jan. 7, 2020, now Pat. No. 11,564,628, which is a
(Continued)

(51) Int. Cl.
A61B 5/00         (2006.01)
A61B 17/00         (2006.01)
(Continued)

(52) U.S. Cl.
CPC .......... A61B 5/6852 (2013.01); A61B 5/6885 (2013.01); A61B 90/06 (2016.02);
(Continued)

(58) Field of Classification Search
CPC ..... A61B 5/6852; A61B 90/06; A61B 5/6885; A61B 2090/064; A61B 2017/00084;
(Continued)

(56)         References Cited

U.S. PATENT DOCUMENTS 4,757,194  A     7/1988  Simms
4,873,989  A     10/1989  Einzig
(Continued)

FOREIGN PATENT DOCUMENTS

DE         3020785 A1     12/1981
DE         3828550 A1     3/1990
(Continued)

OTHER PUBLICATIONS

Written Opinion and International Preliminary Report (PCT/IB2008/ 002675), dated Nov. 24, 2009.
(Continued)

*Primary Examiner* — Patrick Fernandes
(74) *Attorney, Agent, or Firm* — Dentons Durham Jones Pinegar

(57)         ABSTRACT

An ablation catheter system configured with a compact force sensor at a distal end for detection of contact forces exerted on an end effector. The force sensor includes fiber optics operatively coupled with reflecting members on a structural member. In one embodiment, the optical fibers and reflecting members cooperate with the deformable structure to provide a variable gap interferometer for sensing deformation of the structural member due to contact force. In another embodiment, a change in the intensity of the reflected light is detected to measure the deformation. The measured deformations are then used to compute a contact force vector. In some embodiments, the force sensor is configured to passively compensate for temperature changes that otherwise lead to erroneous force indications. In other embodiments,
(Continued)

the system actively compensates for errant force indications caused by temperature changes by measuring certain local temperatures of the structural member.

20 Claims, 8 Drawing Sheets

Related U.S. Application Data division of application No. 13/447,813, filed on Apr. 16, 2012, now Pat. No. 10,561,368.

(60) Provisional application No. 61/475,384, filed on Apr. 14, 2011.

(51) Int. Cl.
    *A61B 90/00*          (2016.01)
    *A61M 25/01*          (2006.01)
    *G01L 1/24*           (2006.01)

(52) U.S. Cl.
    CPC .... *G01L 1/242* (2013.01); *A61B 2017/00084* (2013.01); *A61B 2090/064* (2016.02); *A61B 2562/0266* (2013.01); *A61M 2025/0166* (2013.01); *Y10T 29/49826* (2015.01)

(58) Field of Classification Search
    CPC ........ A61B 2562/0266; A61B 18/1492; A61B 2034/2061; G01L 1/242; G01L 1/246; G01L 11/025; Y10T 29/49826; A61M 2025/0166; G02B 6/29359; G02B 6/02057; G02B 6/022; G02B 6/02042
    See application file for complete search history.

(56)                References Cited

U.S. PATENT DOCUMENTS

| | | | |
|---|---|---|---|
| 4,918,492 A | 4/1990 | Ferdinand |
| 4,966,597 A | 10/1990 | Cosman |
| 4,983,034 A | 1/1991 | Spillman, Jr. |
| 5,014,709 A | 5/1991 | Bjelkhagen |
| 5,018,529 A | 5/1991 | Tenerz |
| 5,065,010 A | 11/1991 | Knute |
| 5,104,392 A | 4/1992 | Kittrell |
| 5,122,137 A | 6/1992 | Lennox |
| 5,178,153 A | 1/1993 | Einzig |
| 5,201,317 A | 4/1993 | Kanazawa |
| 5,202,939 A | 4/1993 | Belleville |
| 5,279,793 A | 1/1994 | Glass |
| 5,289,256 A | 2/1994 | Gramling |
| 5,321,501 A | 6/1994 | Swanson |
| 5,348,019 A | 9/1994 | Sluss, Jr. |
| 5,392,117 A | 2/1995 | Belleville |
| 5,396,887 A | 3/1995 | Imran |
| 5,409,000 A | 4/1995 | Imran |
| 5,423,807 A | 6/1995 | Milder |
| 5,446,546 A | 8/1995 | Breidenbach |
| 5,575,787 A | 11/1996 | Abela |
| 5,594,819 A | 1/1997 | Narendran |
| 5,633,494 A | 5/1997 | Danisch |
| 5,645,065 A | 7/1997 | Shapiro |
| 5,688,267 A | 11/1997 | Panescu |
| 5,693,043 A | 12/1997 | Kittrell |
| 5,696,863 A | 12/1997 | Kleinerman |
| 5,769,847 A | 6/1998 | Panescu |
| 5,798,521 A | 8/1998 | Froggatt |
| 5,807,265 A | 9/1998 | Itoigawa |
| 5,833,688 A | 11/1998 | Sieben |
| 5,844,927 A | 12/1998 | Kringlebotn |
| 5,859,717 A | 1/1999 | Scobey |
| 5,904,658 A | 5/1999 | Niederauer |
| 5,906,614 A | 5/1999 | Stern |
| 5,967,978 A | 10/1999 | Littmann |

| | | | |
|---|---|---|---|
| 6,039,743 A | 3/2000 | Quiachon |
| 6,056,436 A | 5/2000 | Sirkis |
| 6,063,078 A | 5/2000 | Wittkampf |
| 6,102,926 A | 8/2000 | Tartaglia |
| 6,113,590 A | 9/2000 | Fischer |
| 6,113,593 A | 9/2000 | Tu |
| 6,120,476 A | 9/2000 | Fung |
| 6,120,520 A | 9/2000 | Saadat |
| 6,129,667 A | 10/2000 | Dumoulin |
| 6,134,003 A | 10/2000 | Tearney |
| 6,173,091 B1 | 1/2001 | Reich |
| 6,175,669 B1 | 1/2001 | Colston |
| 6,210,346 B1 | 4/2001 | Hall |
| 6,217,574 B1 | 4/2001 | Webster |
| 6,226,542 B1 | 5/2001 | Reisfield |
| 6,256,090 B1 | 7/2001 | Chen |
| 6,262,822 B1 | 7/2001 | Obhi |
| 6,266,551 B1 | 7/2001 | Osadchy |
| 6,272,371 B1 | 8/2001 | Shlomo |
| 6,276,215 B1 | 8/2001 | Berg |
| 6,310,990 B1 | 10/2001 | Putnam |
| 6,324,918 B1 | 12/2001 | Gitis |
| 6,370,412 B1 | 4/2002 | Armoundas |
| 6,398,778 B1 | 6/2002 | Gu |
| 6,425,894 B1 | 7/2002 | Brucker |
| 6,451,009 B1 | 9/2002 | DaSilva |
| 6,458,123 B1 | 10/2002 | Brucker |
| 6,466,811 B1 | 10/2002 | Hassett |
| 6,470,205 B2 | 10/2002 | Bosselmann |
| 6,471,710 B1 | 10/2002 | Bucholtz |
| 6,546,271 B1 | 4/2003 | Reisfeld |
| 6,558,378 B2 | 5/2003 | Sherman |
| 6,563,970 B1 | 5/2003 | Bohnert |
| 6,602,242 B1 | 8/2003 | Fung |
| 6,660,001 B2 | 12/2003 | Gregory |
| 6,674,928 B2 | 1/2004 | Johnson |
| 6,695,808 B2 | 2/2004 | Tom |
| 6,701,931 B2 | 3/2004 | Sliwa, Jr. |
| 6,852,109 B2 | 2/2005 | Winston |
| 6,868,195 B2 | 3/2005 | Fujita |
| 6,898,338 B2 | 5/2005 | Kersey |
| 6,915,048 B2 | 7/2005 | Kersey |
| 6,947,637 B2 | 9/2005 | Smith |
| 6,955,675 B2 | 10/2005 | Jain |
| 7,050,662 B2 | 5/2006 | Behrmann |
| 7,173,713 B2 | 2/2007 | Xu |
| 7,241,986 B2 | 7/2007 | Wang |
| 7,460,964 B2 | 12/2008 | Mizota |
| 7,466,879 B2 | 12/2008 | Tjin |
| 7,491,957 B2 | 2/2009 | Kitamura |
| 7,903,907 B1 | 3/2011 | Park |
| 8,048,063 B2 | 11/2011 | Aeby |
| 8,075,498 B2 | 12/2011 | Leo |
| 8,157,789 B2 | 4/2012 | Leo |
| 2001/0021843 A1 | 9/2001 | Bosselmann |
| 2002/0041722 A1 | 4/2002 | Johnson |
| 2002/0041723 A1 | 4/2002 | Ronnekleiv |
| 2002/0057859 A1 | 5/2002 | Walter |
| 2002/0072680 A1 | 6/2002 | Schock |
| 2003/0219202 A1 | 11/2003 | Loeb et al. |
| 2004/0082844 A1 | 4/2004 | Vardi |
| 2004/0165810 A1 | 8/2004 | Fujita |
| 2004/0206365 A1 | 10/2004 | Knowlton |
| 2004/0243119 A1 | 12/2004 | Lane |
| 2005/0062979 A1 | 3/2005 | Zhu |
| 2005/0213870 A1 | 9/2005 | Kersey |
| 2006/0013523 A1 | 1/2006 | Childlers |
| 2006/0045408 A1 | 3/2006 | Jones |
| 2006/0100610 A1 | 5/2006 | Wallace |
| 2006/0133715 A1 | 6/2006 | Belleville |
| 2006/0200049 A1 | 9/2006 | Leo |
| 2006/0263002 A1 | 11/2006 | Pocha |
| 2007/0014490 A1 | 1/2007 | Silverbrook |
| 2007/0041019 A1 | 2/2007 | Schmidt |
| 2007/0043338 A1 | 2/2007 | Moll |
| 2007/0060847 A1 | 3/2007 | Leo |
| 2007/0065077 A1 | 3/2007 | Childers |
| 2007/0151390 A1 | 7/2007 | Blumenkranz |
| 2007/0151391 A1 | 7/2007 | Larkin |

(56) References Cited

U.S. PATENT DOCUMENTS

| | | |
|---|---|---|
| 2007/0156019 A1 | 7/2007 | Larkin |
| 2007/0265503 A1 | 11/2007 | Schlesinger |
| 2008/0009750 A1 | 1/2008 | Aeby |
| 2008/0159687 A1 | 7/2008 | Donlagic |
| 2008/0294144 A1 | 11/2008 | Leo |
| 2009/0177095 A1 | 7/2009 | Aeby |
| 2009/0287092 A1 | 11/2009 | Leo |
| 2010/0063478 A1 | 3/2010 | Selkee |
| 2010/0087835 A1 | 4/2010 | Blumenkranz |
| 2010/0094163 A1 | 4/2010 | Deladi |
| 2010/0328675 A1 | 12/2010 | Bertholds |
| 2011/0087112 A1 | 4/2011 | Leo |
| 2012/0078138 A1 | 3/2012 | Leo |
| 2012/0265102 A1 | 10/2012 | Leo |

FOREIGN PATENT DOCUMENTS

| | | |
|---|---|---|
| EP | 0934728 A2 | 8/1999 |
| EP | 2047797 A2 | 4/2009 |
| JP | H09297078 A | 11/1997 |
| JP | H10137200 A | 5/1998 |
| JP | 2000227367 A | 8/2000 |
| JP | 2004251779 A | 9/2004 |
| WO | 9738637 A1 | 10/1997 |
| WO | 9819044 A1 | 5/1998 |
| WO | 9945994 A1 | 9/1999 |
| WO | 0133165 A1 | 5/2001 |
| WO | 0174252 A2 | 10/2001 |
| WO | 0219898 A2 | 3/2002 |
| WO | 0219903 A1 | 3/2002 |
| WO | 0223148 A1 | 3/2002 |
| WO | 0247751 A2 | 6/2002 |
| WO | 2004002303 A1 | 1/2004 |
| WO | 2005059510 A2 | 6/2005 |
| WO | 2006092707 A1 | 9/2006 |
| WO | 2007015139 A2 | 2/2007 |
| WO | 2007050960 A2 | 5/2007 |
| WO | 2007111737 A2 | 10/2007 |
| WO | 2008000246 A2 | 1/2008 |
| WO | 2008003307 A2 | 1/2008 |
| WO | 2008045958 A2 | 4/2008 |
| WO | 2009114955 A1 | 9/2009 |
| WO | 2010079418 A1 | 7/2010 |

OTHER PUBLICATIONS

International Search Report (PCT/IB2010/000021), dated May 27, 2010.

FISO, "FOS-N Strain Sensor," FISO Technologies Inc., (2006), Canada.

Dickmann, "Experiment 03, Fabry Perot Resonator," (2003), pp. 1-19.

Precision Photonics Corporation, "Basic Physics and Design of Etalons," (2003), pp. 1-5.

Luna Innovations, "EFPI Techniques for Strain and Displacement Sensing," (Aug. 1999).

Luna Innovations, "Fiber Optic Bragg Grating Sensor," www.lunainnovations.com/products/shape.asp, (Aug. 2005).

Meller, "Extrinsic Fabry-Perot Interferometer System Using Wavelength Modulated Source," (Dec. 1996).

FISO Technologies, "Technical Note, Principle of Fiber-Optic Sensors," (received prior to Feb. 20, 2007).

Uffelen, "Anchoring points for fibre optic strain sensors," Optical Techniques for Smart Structures and Structural Monitoring, (Feb. 1997), London, UK. Abstract.

Lo, "Using in-fiber Bragg-grating sensors for measuring axial strain and temperature simultaneously on surfaces of structures," Optical Engineering, (Aug. 1998) vol. 37, Issue 8, pp. 2272-2276. Abstract.

DuPont, "DuPont Zenite LCP liquid crystal polymer resin," Product and Property Guide, K-15415, May 2006.

Yokoyama, Md, et al., "Novel Radiofrequency Ablation Catheter with Contact Force Sensor Predicts Lesion Size and Incidence of Steam Pop in Canine Model," Heart Rhythm Society, May 2007, Denver USA, vol. 4, Issue 5.

Shah et al., "Evaluation of a New Catheter Sensor for Real-Time Measurement of Tissue Contact," Heart Rhythm Society, May 2006, Boston, USA, vol. 3, Issue 5.

"The Unique Force Sensor Ablation Catheter," www.endosense. com/site/product.htm, Mar. 2007.

European Office Action from European Application No. 06795186.3 dated Aug. 9, 2011.

European Office Action from European Application No. 11158967.7 dated Aug. 10, 2011.

Notice of Reasons for Rejection (translation) from Japanese Application No. 2007-557615 mailing date: Sep. 13, 2011.

International Preliminary Report on Patentability and Written Opinion from International Application No. PCT/IB2009/051967 date of issuance Nov. 17, 2010.

Application and File History for U.S. Appl. No. 13/308,196, filed Nov. 30, 2011, inventors Leo et al.

European Office Action for European Application No. 11158967.7-1654 dated Mar. 12, 2013.

Notification of the Second Chinese Office Action for Chinese Application No. 200980125027.0 dated Mar. 12, 2013. English Translation is provided.

European Office Action for European Application No. 08826173.0-1265 dated Oct. 1, 2012.

European Office Action for European Application No. 06795186.3-2310 dated Oct. 18, 2012.

Notification of the First Office Action of Chinese Office Action for Chinese Application No. 200980125027.0 dated Jun. 29, 2012.

Japanese Interrogatory for Japanese Application No. 2007/557615 dated Oct. 29, 2012.

Japanese Notification of Reasons for Rejection for Japanese Application No. 2011509074 dated May 28, 2013.

Written Opinion and International Searching Authority for International Application No. PCT/US2012/033791 dated Aug. 13, 2012.

Application and File History for U.S. Appl. No. 11/237,053, filed Sep. 28, 2005, inventor Leo et al.

Application and File History for U.S. Appl. No. 11/450,072, filed Jun. 9, 2006, inventor Aeby.

Application and File History for U.S. Appl. No. 12/352,426, filed Jan. 12, 2009, inventor Aeby.

Application and File History for U.S. Appl. No. 12/152,473, filed May 14, 2008, inventor Leo.

Application and File History for U.S. Appl. No. 13/096,647, filed Apr. 28, 2011, inventor Leo.

Application and File History for U.S. Appl. No. 13/179,076, filed Jul. 8, 2011.

Application and File History for U.S. Appl. No. 11/989,902, filed Jan. 2, 2008, inventor Leo.

Notification of the First Office Action for Chinese Application No. 20068007106.8 dated May 8, 2009.

Fernandez et al., "Multi-component force sensor based on multiplexed Fibre Bragg grating strain sensors" Measurement Science and Technology (2001) 810-813.

Paris-Seeley et al., "A compliance-independent pressure transducer for biomedical device-tissue interfaces," Biomed Instrum Technol. Nov.-Dec. 2000; 34(6): 423-31. Abstract.

Brown, "Development of a Brillouin scattering based distributed fibre optic strain sensor," 2001.

Barrett, et al., "Extrinsic Fabry-Perot interferometer for measuring the stiffness of ciliary bundles on hair cells," Trans Biomed Eng. Mar. 1999; 46(3):331-9. Abstract.

Erdimer et al., "Fiberoptic measurement of tendon forces is influenced by skin movement artifact," J Biomech. Mar. 2003; 36(3): 449-55. Abstract.

Schmidt et al., "Fiber-Optic Extrinsic Fabry-Perot Interferometer Strain Sensor with 50pm displacement resolution using three-wavelength digital phase demodulation," Optics Express, Apr. 9, 2001, vol. 8, No. 8.

"Fiber-optic strain-monitoring technology: BOTDR Brillouin Optical Timedomain Reflectometer," NTT Innovative Technology Site. Jul. 18, 2005.

(56)          References Cited

OTHER PUBLICATIONS

Fearn et al., "An optical fiber transducer for single myofibril force measurement," Trans Biomed Eng. Nov. 1993; 40(11): 1127-32. Abstract.

Komi et al., "Optic fibre as a transducer of tendomuscular forces," Eur J Appl Physiol 1996;72(3):278-80. Abstract.

Del Villar et al., "Optimization of sensitivity in Long Period Fiber Gratings with overlay deposition," Optics Express, Jan. 10, 2005, vol. 13, No. 1.

Barb et al., "Versatile, high-speed force transducer using a laser fiode beam as an optical lever," J Appl Physiol 88: 308-314, 2000.

Rao, "Recent progress in applications of in-fibre Bragg grating sensors," Optics and Lasers in Engineering, vol. 31, Iss. 4, Apr. 1999, pp. 297-324. Abstract.

Inaudi, "Application of optical fiber sensor in civil structural monitoring," The International Society for Optical Engineering, 2003. Abstract.

Peirs et al., "Design of an Optical Force Sensor for Force Feedback during Minimally Invasive Robotic Surgery" 2003. Katholieke Univ. Leuven Belgium.

Zhang et al., "On SDM/WDM FBG Sensor Net for Shape Detection of Endoscope," Proceedings of the IEEE International Conference on Mechatronics Automation, Jul. 2005.

Park et al, Force Sensing Robot Fingers using Embedded Fiber Bragg Grating Sensors and Shape Deposition Manufacturing. Santa Clara, CA 2007.

Endosense receives CE mark for Tacticath force-sensing ablation catheter, May 4, 2009.

"Endosense launches TOCCATA clinical study" Oct. 7, 2008.

"Endosense achieves ISO 13485 certification" Aug. 12, 2008.

"Endosense unveils five groundbreaking abstracts on contact force measurement for catheter ablation" May 13, 2008.

Fuster et al., "ACC/AHA/ESC 2006 Guidelines for the Management of Patients with Atrial Fibrillation," Circulation Journal of the American Heart Association, 2006, Dallas, Texas, pp. e319-e321.

Calkins et al., "HRS/EHRA/ECAS Expert Consensus Statement on Catheter and Surgical Ablation of Atrial Fibrillation: Recommendations for Personnel, Policy, Procedures and Follow-Up," Eurospace (2007).

Natale et al., "Venice Chart International Consensus Document on Atrial Fibrillation Ablation," Journal of Cardiovascular Electrophysiology, vol. 18. No. 5, May 2007.

Cappato et al., "Worldwide Survey on the Methods, Efficacy, and Safety of Catheter Ablation for Human Atrial Fibrillation," Journal of the American Heart Association, 2005.

Hasin et al., "Miniature Force Transducer for Myocardial Stimulation and Local Tension Measurements," IEEE Transactions on Biomedical Engineering, vol. BME-26, No. 2, Feb. 1979.

"Sensei X Robotic Catheter System for Electrophysiology Procedures," MedGadget, Sep. 18, 2009.

"Intellisense Fine Force Technology," Hansen Medical (website), http://www.hansenmedical.com/products/intellisense.aspx Sep. 22, 1999.

Hansen Medical product brochure, Sensie Robotic Catheter System. 2009.

Hansen Medical product brochure, Artisan extend Control Catheter. 2009.

Peirs et al., "A micro optical force sensor for force feedback during minimally invasive robotic surgery," Sensors and Actuators A 115 (2004) 447-455.

Xiao et al., "Fiber optic pressure sensor with self-compensation capability for harsh environment applications," Optical Engineering May 2005, vol. 44(5).

European Office Action for European Application No. 06795186.3 dated Nov. 25, 2010.

European Office Action for European Application No. 06710474.5 dated Feb. 16, 2009.

European Office Action for European Application No. 06710474.5 dated Aug. 24, 2009.

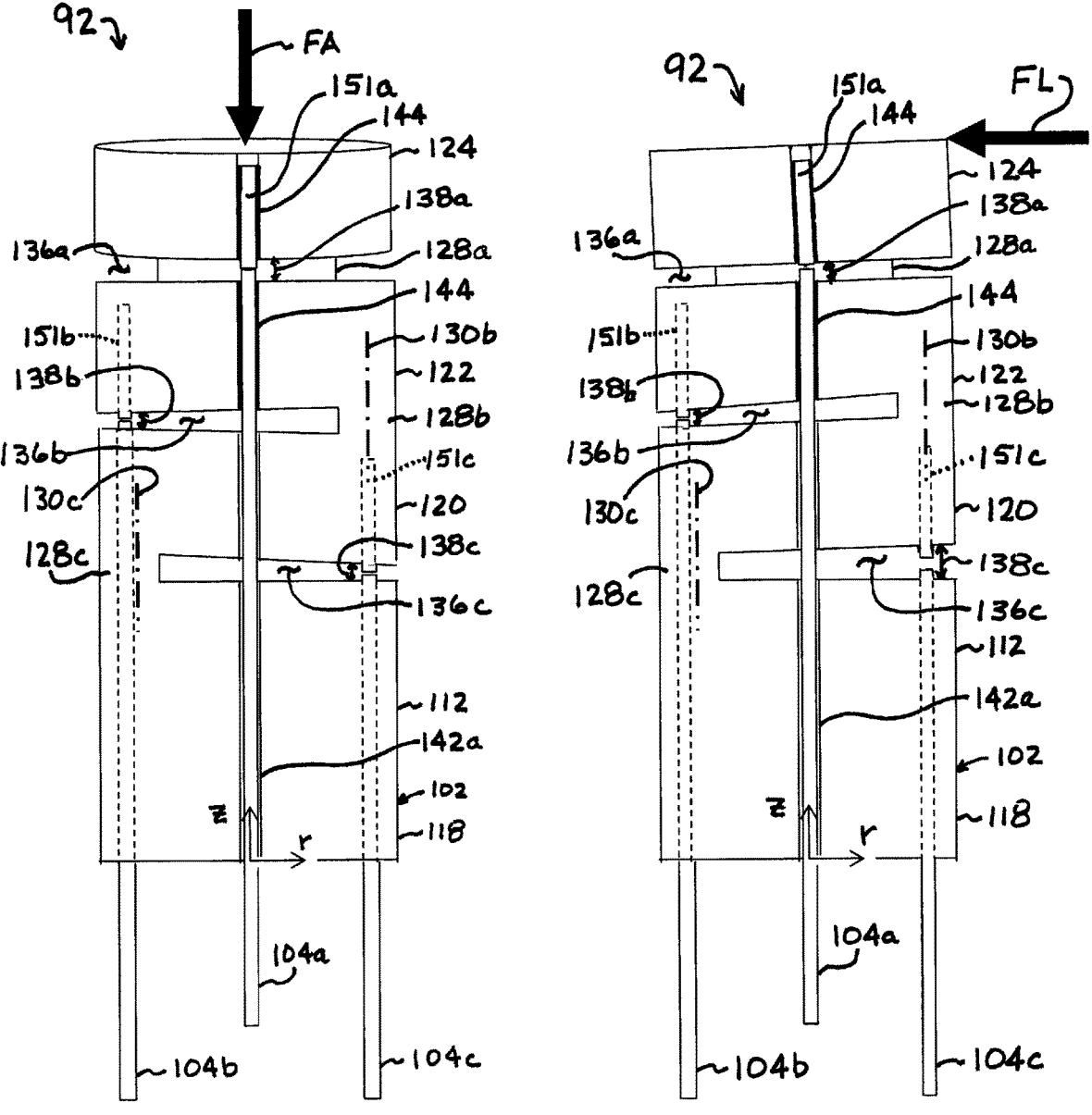
FIG. 12A                    FIG. 12B

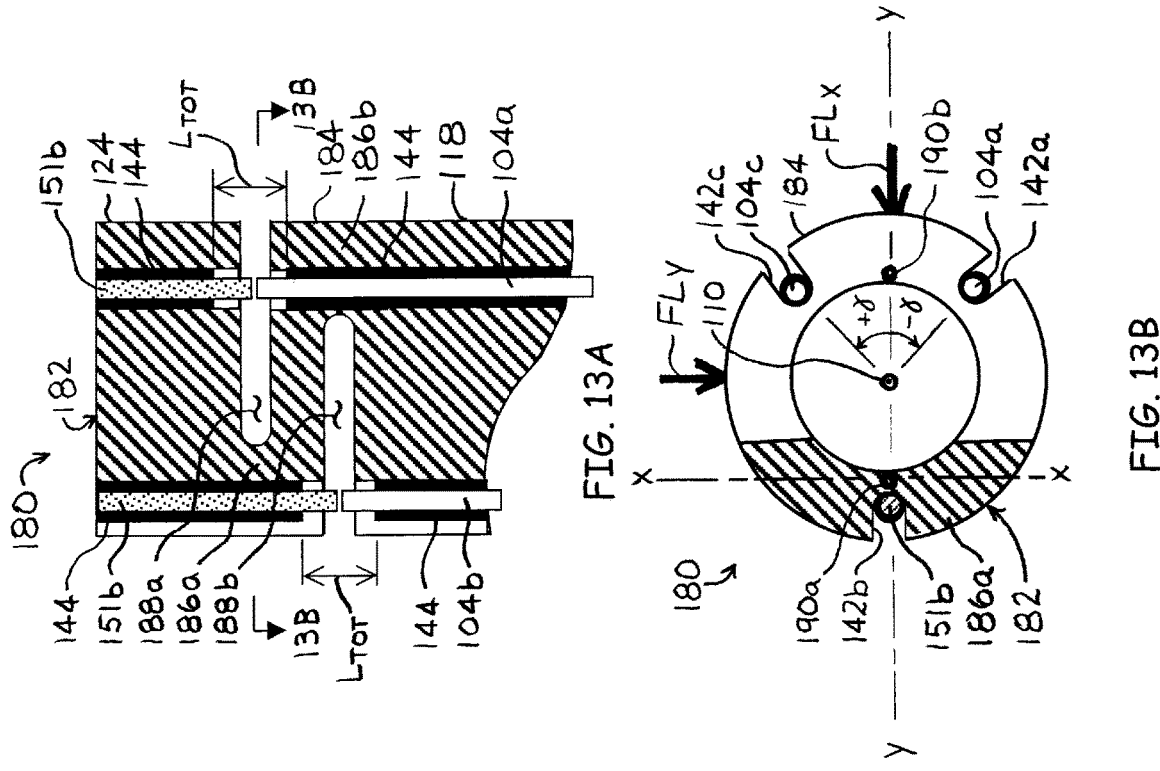
FIG. 13A
FIG. 13B
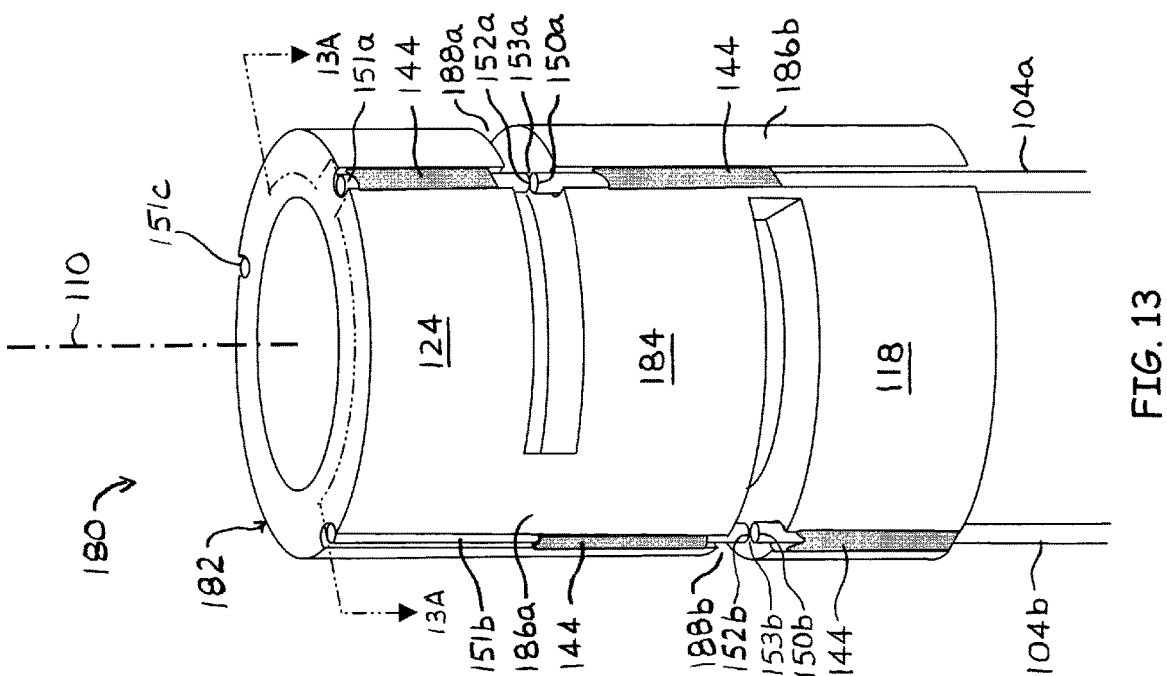
FIG. 13

COMPACT FORCE SENSOR FOR CATHETERS

CROSS REFERENCE OF RELATED APPLICATION

This application is a continuation of U.S. patent application Ser. No. 16/736,570, filed Jan. 7, 2020, which is a divisional application of U.S. patent application Ser. No. 13/447,813, filed Apr. 16, 2012, which claims benefit of U.S. Provisional Application Ser. No. 61/475,384, filed Apr. 14, 2011, all of which are incorporated by reference in their entirety.

FIELD OF THE INVENTION

The disclosed invention relates generally to force sensing devices capable of resolving the magnitude and direction of a force vector. More specifically, the invention relates to a force sensing tip to aid in the positioning of catheters used in humans or animals, or for serving as feedback elements in robotic surgical systems.

BACKGROUND

For many years, exploration and treatment of various organs or vessels has been possible using catheter-based diagnostic and treatment systems. Such catheters are introduced through a vessel leading to the cavity of the organ to be explored or treated or alternatively can be introduced directly through an incision made in the wall of the organ. In this manner, the patient avoids the trauma and extended recuperation times typically associated with open surgical procedures.

To provide effective diagnosis or therapy, it is frequently necessary to first map the zone to be treated with great precision. Such mapping can be performed, for example, when it is desired to selectively ablate current pathways within a heart to treat atrial fibrillation. Often, the mapping procedure is complicated by difficulties in locating the zone(s) to be treated due to periodic movement of the heart throughout the cardiac cycle.

Previously-known systems for mapping the interior of a vessel or organ are described, for example, in U.S. Pat. Nos. 6,546,271 and 6,226,542. The catheters described in those patents employ electromagnetic, electrical, magnetic or acoustic sensors to map the position of a distal end of the catheter in space and then construct a three-dimensional visualization of the vessel or organ interior.

One drawback of such previously known mapping systems is that they rely on manual feedback of the catheter and/or impedance measurements to determine when the catheter is properly positioned in the vessel or organ. Those systems do not measure contact forces with the vessel or organ wall or detect contact forces applied by the catheter against the organ or vessel wall that can modify the true wall location. Instead, previously known mapping methods are time-consuming, dependent upon the skill of the clinician, and cannot compensate for artifacts created by excessive contact forces.

Once the topography of the vessel or organ is mapped, either the same or a different catheter can be employed to effect treatment. Depending upon the specific treatment to be applied to the vessel or organ, the catheter may comprise any of a number of end effectors, such as but not limited to RF ablation electrodes, rotary or scissor action cutting heads, laser ablation system, injection or sewing needles, fluid conveyance systems, forceps, manipulators, mapping electrodes, endoscopic vision systems and therapeutic delivery systems such as genetic impregnation devices. Exemplary systems are described, for example, in U.S. Pat. Nos. 6,120,520, 6,102,926, 5,575,787, 5,409,000 and 5,423,807.

The effectiveness of such end effectors often depends on having the end effector in contact with the tissue of the wall of the organ or vessel. Many previously-known treatment systems include expandable baskets or hooks that stabilize the distal extremity of the catheter in contact with the tissue. Such arrangements, however, can be inherently imprecise due to the motion of the organ or vessel. Moreover, the previously-known systems do not provide the ability to sense the load applied to the distal extremity of the catheter by movement of the tissue wall.

For example, in the case of a cardiac ablation system, at one extreme the creation of a gap between the end effector of the treatment system and the tissue wall can render the treatment ineffective, and inadequately ablate the tissue zone. At the other extreme, if the end effector of the catheter contacts the tissue wall with excessive force, inadvertent puncturing of the tissue resulting in cardiac tamponade can occur.

U.S. Pat. No. 6,695,808 proposes several solutions to measure the force vector arising from contact with the tissue surface, including mechanical, capacitive, inductive and resistive pressure sensing devices. One drawback of such devices, however, is that they are relatively complex and must be sealed to prevent blood or other liquids from disturbing the measurements. In addition, such load sensing devices can result in an increase in the insertion profile of the distal extremity of the catheter. Still further, sensors of the types described in that patent may be subject to electromagnetic interference.

One previously-known solution for dealing with potential electromagnetic interference in the medical environment is to use light-based systems rather than electrical measurement systems. One such light-based system is described in U.S. Pat. No. 6,470,205 to Bosselman which describes a robotic system for performing surgery comprising a series of rigid links coupled by articulated joints. A plurality of Bragg gratings are disposed at the articulated joints so that the bend angle of each joint may be determined optically, for example, by measuring the change in the wavelength of light reflected by the Bragg gratings using an interferometer.

International Publication No. WO 01/33165 to Bucholtz describes an alternative spatial orientation system wherein wavelength changes measured in a triad of optical fiber strain sensors are used to compute the spatial orientation of a catheter or other medical instrument. Although Bucholtz discloses that the strain sensors may be encased within a deformable sheath, as is also described in Bosselman, calculation of the bend angles is not described as requiring characterization of the material properties of the deformable sheath.

Recent advances in catheter technology have included the use of fiber optic force sensors to detect the reactive force at the distal extremity of an end effector when placed in contact with the interior wall of a vessel or organ. For example, an article by J. Peirs et al., entitled "Design of an Optical Force Sensor for Force Feedback during Minimally Invasive Robotic Surgery," published by Katholieke Universiteit Leuven, Belgium, describes a tri-axial force sensor for use generating force feedback systems in a robotic surgery system. The apparatus includes a plurality of optical fibers that direct light onto a mirrored surface disposed adjacent to a distal tip of the device. The intensity of the light reflected from the mirrored surface is measured and may be correlated to the force required to impose a predetermined amount of flexure to the distal tip. The article describes a flexible and compact structure that may be used to produce variations in light intensity responsive to contact forces that deform the structure.

International Publication No. WO 2007/015139 to Leo, et al. (Leo '139), discloses a device and method for resolving a force vector (magnitude and direction) applied to the distal end of a catheter. Leo '139 discloses the use of fiber optic strain elements in a catheter that maintains essentially the same profile as with catheters that do not sense touching forces and is substantially immune to electromagnetic interference. U.S. Pat. No. 8,075,498 to Leo et al. (Leo '498) discloses a force sensing catheter system that utilizes the deformation of fiber Bragg grating strain sensors to infer the force incident upon the tip of the catheter. U.S. Pat. No. 8,048,063 to Aeby et al. (Aeby '063) discloses a tri-axial force sensor having a deformable structure that isolates the deflections caused by forces imposed on the distal end of the catheter and wherein fiber optics both irradiate and receive reflected light from the deformable structure, with intensities of the received reflected light varying according to the imposed force. United States Patent Application No. 2009/0287092 to Leo et al. (Leo '092) discloses a fiber optic touch sensing catheter that incorporates multiple temperature sensors for active compensation of the effects caused by temperature changes, including a calibration technique for reducing thermally induced errors. U.S. Pat. No. 8,157,789 to Leo et al. (Leo '789) discloses a fiber optic touch sensing catheter that utilizes an interferometric principle to detect structural deformations of a strain sensing assembly to infer forces. International Publication Nos. WO 2010/079418 to Leo et al. (Leo '418) and WO 2009/114955 to Kistler et al. (Kistler) disclose catheter-based force sensors having a structural member that deflect rotationally about flexural portions to enhance the sensitivity in response to a contact force.

While Kistler presents a design that can be made more compact than the devices disclosed by Leo, it suffers from thermally induced error and non-uniform (directionally dependent) sensitivity. In addition, the tri-axial force sensors of Aeby '063 tend to involve complex machining and fabrication to achieve the desired isolation effect.

Accordingly, it would be desirable to provide diagnostic and treatment apparatus, such as a catheter or guide wire, that permits sensing of loads applied to a distal extremity of the apparatus, but which do not substantially increase the insertion profile of the apparatus. It is further desirable to provide diagnostic and treatment apparatus, such as a catheter and guide wire, that permits computation of forces applied to a distal extremity of the apparatus, and which are substantially immune to electromagnetic interference. A fiber optic touch sensing catheter that combines compactness, high sensitivity (high resolution) and relative insensitivity to temperature change, all while being relatively easy to fabricate, would be a welcome advance in the field of minimally invasive surgery.

SUMMARY OF THE INVENTION

Various embodiments of the invention include a catheter system configured with a compact force sensor at a distal end for detection of contact forces exerted on an end effector. In one embodiment, the sensitivity is both increased and made more uniform over the compact designs of the prior art. For ablation applications, the temperature drift of the force sensor can reach 20 Kelvins. Accordingly, in some embodiments, the force sensor is configured to passively compensate for these temperature changes to limit the errant force indications. In other embodiments, the system actively compensates for errant force indications caused by temperature changes in the force sensor by measuring certain local temperatures of the force sensor.

Leo '789 discloses a force sensor that, through the matching of the coefficient of thermal expansion (CTE) of structural members with the CTE of the fiber optics, is substantially insensitive to temperature change. Leo '789 also discloses configurations of the force sensor that mechanically amplifies the detected deflection due to an applied distal end force, thus increasing the sensitivity of the force sensor.

Leo '418, and particularly Kistler, discloses force sensors that can be more compact than the force sensor of Leo '789 and with generally the same sensitivity to contact force as Leo '789. Compactness provides enhanced maneuverability both en route to and at the target site. However, due the materials of construction, the Kistler and Leo '418 devices are subject to greater thermally-induced error than the device of Leo '789. The device disclosed by Kistler is also prone to unequal sensitivities between sensing elements, i.e., the displacement at one sensing element per unit force is different from that of another sensing element. This can cause differing sensitivity and attendant uncertainty that depends on the direction of the force.

Embodiments of the invention disclosed herein provide the compactness of the Kistler device while reducing the thermally induced error. Some embodiments provide for a more uniform response between force sensing elements.

Structurally, in various embodiments, the force sensor includes a structural member having axially aligned segments that define slots therebetween, each slot being bridged by a flexure. In response to a contact force applied distal to the structural member, the structural member flexes about the flexures, causing the slots to change in dimension. A plurality of fiber optics are mounted to the structural member so that the distal end of a given fiber is proximate a given slot. A plurality of reflecting members are arranged to oppose the distal ends of the fiber optics, each reflecting member opposing a corresponding one of the fiber optics to define a gap therebetween. The gaps create a plurality of interferometric cavities that change congruently with the change in the slot dimension in response to the contact force.

In one embodiment, a force sensor for use at a distal tip of a catheter includes a structural member that defines a longitudinal axis and includes a first segment and a second segment that are adjacent each other along the longitudinal axis, the first and second segments defining a first slot therebetween that is bridged by a first flexure. A third segment is adjacent the second segment along the longitudinal axis, the second and third segments defining a second slot therebetween, the second slot being bridged by a second flexure. A plurality of fiber optics operatively is coupled with the structural member, each of the plurality of fiber optics having a distal end that is proximate a corresponding reflecting member to define a respective gap therebetween. The reflecting member extends from the third segment of the structural member. In one embodiment, each of the respective gaps is disposed proximate the second slot, each of the plurality of fiber optics being oriented to emit light across the respective gap and onto the corresponding reflecting member. The fiber optics can be affixed to the first segment and pass through the second segment. The structural member can be configured to produce a change in the dimension of at least one of the respective gaps in response to a force exerted on the distal tip of the catheter. The distal ends of the plurality of fiber optics can be adapted for collection of at least a portion of the light reflected from the corresponding reflecting member. In one embodiment, the structural member is a hollow tube which can have a circular cross-section in a plane orthogonal to the longitudinal axis. The plurality of fiber optics can number at least three. In one embodiment, each of the respective gaps is a Fabry-Perot resonator.

The first flexure of the force sensor can be centered about a first flexural axis that is parallel to the longitudinal axis, and the second flexure is centered about a second flexural axis that is parallel to the longitudinal axis. In one embodiment, the first flexural axis, the second flexural axis and the longitudinal axis are substantially coplanar.

Some embodiments of the invention include at least one of the fiber optic that is spliced with the corresponding reflecting member, the gap being defined by a cavity defined between the fiber optic and the corresponding reflecting member.

Various embodiments implement "active" temperature compensation, wherein temperatures of the structural member are measured for the purpose of determining the effect of thermal expansion/contraction. These embodiments can include at least two temperature sensors, each configured to detect a temperature of the structural member. In one embodiment, a first of the at least two temperature sensors are centered substantially at the interface of the first flexure and the second segment, and a second of the at least two temperature sensors is centered substantially at the interface of the second flexure and the second segment. In one embodiment, each flexure is instrumented with a temperature sensor.

Other embodiments implement "passive" temperature compensation, including means for passively compensating for changes in the dimensions of the respective gaps that are caused by temperature changes without measuring the temperature of the body. In some embodiments, a passive compensation catheter system comprises a flexible, elongate catheter assembly having a proximal portion, a distal portion and a middle portion. An end effector can be operatively coupled with the distal portion of the catheter assembly. A fiber optic force sensing assembly is operatively coupled with the distal portion of the catheter assembly, the fiber optic force sensing assembly including a structural member that defines a displacement dimension responsive to a contact force exerted on the end effector. The system can also further include at least one of a power source, an electromagnetic source, a data acquisition device and a control system operatively coupled with the elongate catheter assembly.

Certain passive temperature compensation embodiments include corresponding reflecting members that comprise a material having a coefficient of thermal expansion that differs from the fiber optics. The material of the corresponding reflecting members can be one of metallic doped fiber optic and a sapphire fiber.

In one embodiment, the passively compensating force sensing assembly includes a structural member, a plurality of reflecting members, each affixed to and extending from the structural member and each including a reflective surface, and a plurality of fiber optics, each paired with a corresponding one of the plurality of reflecting members and each oriented and adapted to irradiate the reflective surface of the corresponding one of the plurality of reflecting members and to collect at least a portion of the light reflected from the proximal end of the corresponding reflecting member, each paired fiber optic and reflecting member defining a corresponding gap therebetween. The plurality of reflecting members comprise a material having a coefficient of thermal expansion that differs from that of the plurality of fiber optics, the coefficient of thermal expansion of the reflecting member being selected for passive compensation of changes in the corresponding gaps between each paired fiber optic and reflecting member that are caused by temperature change. The plurality of fiber optics can be affixed to the structural member, and can comprise a material having a coefficient of thermal expansion that differs from that of the structural member.

In various embodiments, the structural member defines a longitudinal axis and includes a plurality of segments that are sequentially adjacent each other in a serial arrangement along the longitudinal axis, the segments being bridged by flexures located between adjacent of the segments. The plurality of segments define a plurality of slots located between adjacent of the plurality of segments and being bridged by a corresponding one of the plurality of flexures. The structural member includes an outer surface, and, in one embodiment, each of the flexures defines a portion of the outer surface of the structural member.

In one embodiment, the corresponding gap defined by the paired fiber optic and the reflecting member is located within one of the plurality of slots. In various embodiments, a plurality of the corresponding gaps defined by the paired fiber optics and reflecting members are located within a common one of the plurality of slots. The plurality of reflecting members can all be proximate one of the plurality of slots, the one of the plurality of slots being the distal-most of the plurality of slots.

Alternatively, the one of the plurality of slots can be the proximal-most of the plurality of slots, and the plurality of reflecting members and the structural member can have the same coefficient of thermal expansion. The plurality of fiber optics can also be affixed to a proximal-most of the plurality of segments and extend so that the corresponding gaps of the paired fiber optics and the reflecting members are proximate the proximal-most of the plurality of slots. Each of the plurality of fiber optics can be adapted to emit light onto the proximal end of the corresponding reflecting member.

In another embodiment, a method of making a force sensor for a catheter comprises providing a structural member having a reflecting member and arranging a distal end of a fiber optic opposite the reflecting member. The fiber optic and the reflecting member define a distance therebetween, the distance being within a range of predetermined values and being responsive to a force exerted on the structural member. The reflecting member can have a coefficient of thermal expansion that compensates for changes in the distance between the fiber optic and the reflecting member that are caused by temperature changes to the structure and the reflecting member.

In one embodiment, a method of actively compensating for thermally induced errors in a fiber optic force sensing assembly includes providing a structural member including a first segment and a second segment defining a separation therebetween, the separation being bridged by a flexural member, the second segment including a reflecting member. A fiber optic having a distal end is affixed to the first segment, the distal end being oriented to define a gap between the distal end and the reflecting member. In one embodiment, the flexural member and the affixed fiber optic are diametrically opposed. The flexural member can be instrumented with a temperature sensor. In one embodiment, a temperature sensing module operatively coupled with a microprocessor is provided, the temperature sensing module adapted to receive signals from the temperature sensor, the microprocessor being operatively coupled with a computer-readable storage device. The computer-readable storage device can be configured to include instructions for the microprocessor, the instructions comprising:

receiving information from the temperature sensing module based on signals received from the temperature sensor;

determining a temperature change of the flexure based on the information, the temperature change being relative to a reference temperature; and inferring a change in the gap based on the temperature change of the flexure.

BRIEF DESCRIPTION OF THE DRAWINGS

FIGS. 12A and 12B depict the deflection of the fiber optic force sensing assembly of FIG. 5 under an axial load and a lateral load, respectively;

FIG. 13 is an enlarged perspective view of a fiber optic force sensing assembly in a embodiment of the invention;

FIGS. 13A and 13B are sectional views of the force sensing assembly of FIG. 13;

DETAILED DESCRIPTION

Figures 1, 2A, 2B:
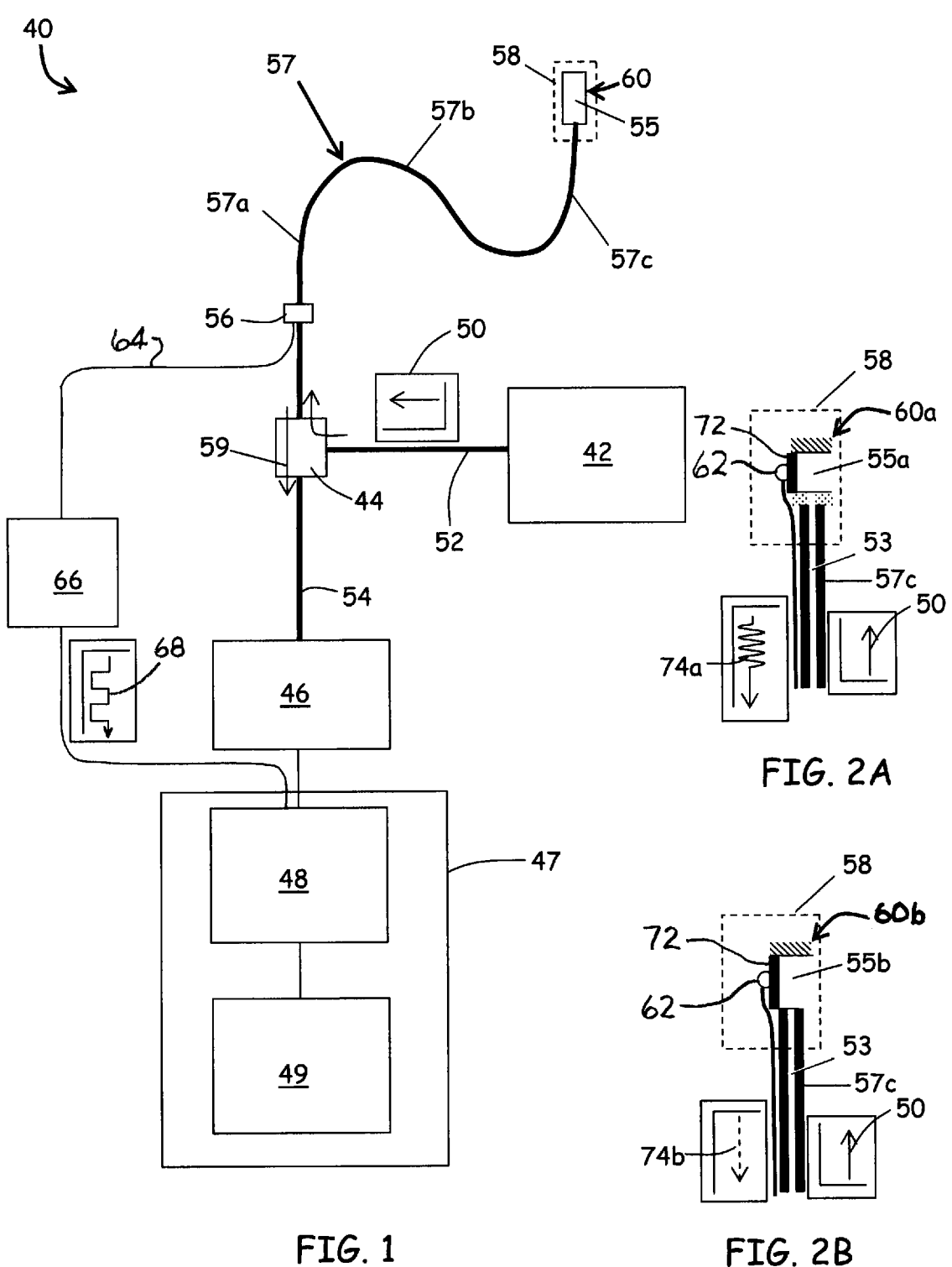
FIG. 1 is a block diagram of a strain sensing system in an embodiment of the invention.
FIG. 2A is a schematic depiction of an interferometric fiber optic sensor in an embodiment of the invention.
FIG. 2B is a schematic depiction of an intensity varying fiber optic sensor in an embodiment of the invention.

Referring to FIG. 1, an embodiment of a displacement sensing system 40 is depicted in accordance with the invention. The displacement sensing system 40 can comprise an electromagnetic source 42, a coupler 44, a receiver 46, an operator console 47 operatively coupled with a microprocessor 48 and a computer-readable storage device 49. The electromagnetic source 42 outputs a transmitted radiation 50 of electromagnetic radiation that is substantially steady state in nature, such as a laser or a broadband light source. A transmission line 52 such as a fiber optic cable carries the transmitted radiation 50 to the coupler 44, which directs the transmitted radiation 50 through a transmitting/receiving line 54 and through a fiber optic element 53 (FIG. 2A) contained within a flexible, elongate catheter assembly 57 to a fiber optic sensing element 60. The fiber optic element 53 of the catheter assembly 57 and transmitting/receiving line 54 can be coupled through a connector 56 as depicted in FIG. 1.

The catheter assembly 57 can have a width and a length suitable for insertion into a bodily vessel or organ. In one embodiment, the catheter assembly 57 comprises a proximal portion 57a, a middle portion 57b and a distal portion 57c. The distal portion 57c can include an end effector 58 that houses the fiber optic sensing element 60. The catheter assembly 57 can be of a hollow construction (i.e., having a lumen) or of a non-hollow construction (i.e., no lumen), depending on the application. In various embodiments of the invention, the catheter assembly 57 includes a gap 55 that is responsive to a contact force exerted on the end effector 58.

In one embodiment, a temperature sensor 62 (FIG. 2A) is routed through the catheter assembly 57, with a lead line 64 that exits the connector 56. The lead line 64 can be routed to a temperature sensing module 66 that conditions the signal received from the temperature sensor 62 and converts it to a digital signal 68. The digital signal 68 can then be routed to the microprocessor 48 for processing.

Referring to FIG. 2A, an interferometric fiber optic sensing element 60a is depicted as the fiber optic sensing element 60 in an embodiment of the invention. In this embodiment, the transmitted radiation 50 enters an interferometric gap 55a, which is defined by a structural member 72. In one embodiment, the temperature sensor 62 is arranged to sense the temperature of the structural member 72 A portion of the radiation that enters the interferometric gap 55a is returned to the fiber optic element 53 of the catheter assembly 57 as reflected radiation 74 that defines a modulated waveform 74a created, for example, by the multiple interreflection principle of a Fabry-Perot resonator. More discussion of the interferometric principle is found attendant to the discussion of FIG. 6A below.

Referring to FIG. 2B, an intensity-varying fiber optic sensing arrangement 60b is depicted as the fiber optic sensing element 60 in an embodiment of the invention. In this embodiment, the transmitted radiation 50 enters an intensity-varying gap 55b, a portion of which is reflected back to fiber optic element 53. The intensity of the reflected radiation 74b received by the fiber optic element 53 varies inversely with the dimension of the intensity-varying gap 55b.

The reflected radiation 74 can be transmitted back through the transmitting/receiving line 54 to the receiver 46. The displacement sensing system 40 can interrogate the displacement sensing element 60 at an exemplary and non-limiting rate of 10-Hz. The receiver 46 is selected to detect a characteristic of the reflected radiation 74 corresponding to the dimension of the gap 55 (i.e., the frequency of the modulated waveform 74a or the intensity of the reflected light 74b). The receiver 46 manipulates and/or converts the incoming reflected radiation 74 into digital signals for processing by the microprocessor 48.

Figure 3:
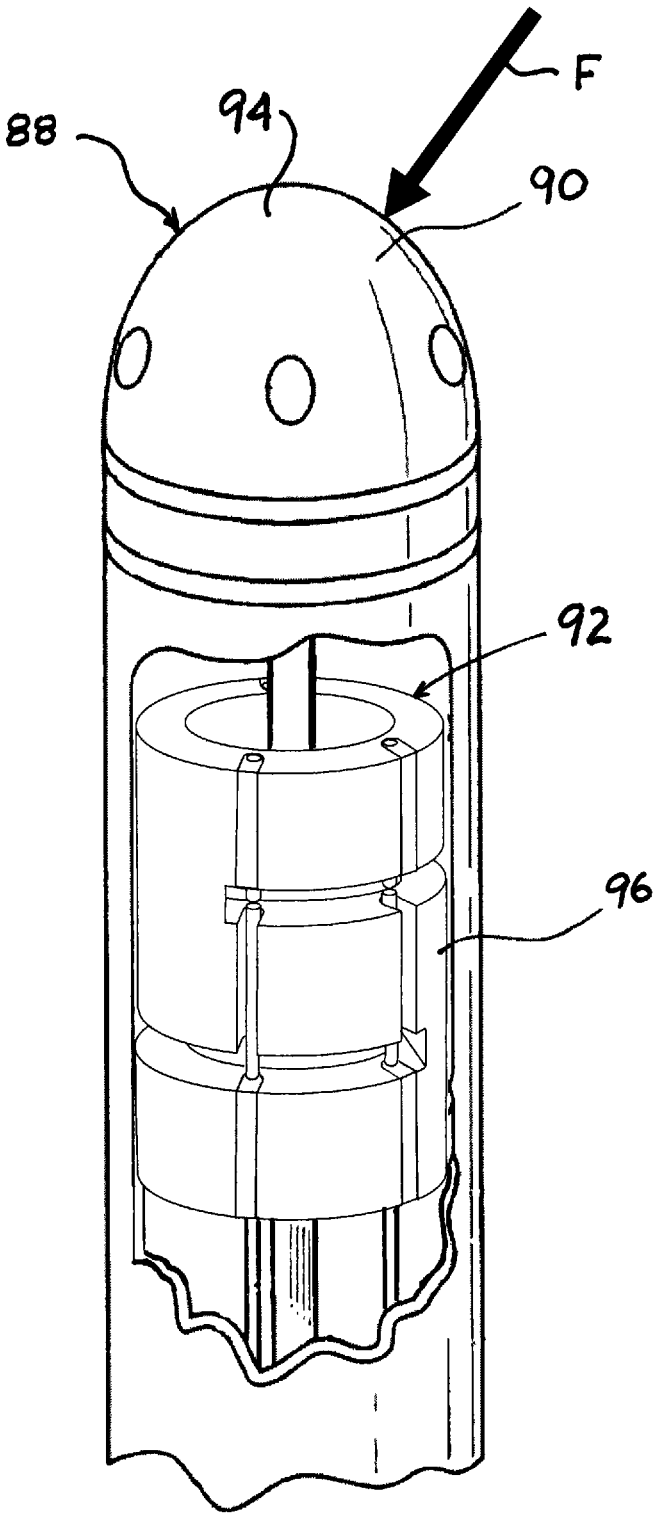
FIG. 3 is a partial cutaway view of a distal portion of a catheter assembly having a fiber optic force sensing assembly in an embodiment of the invention.
Figure 5:
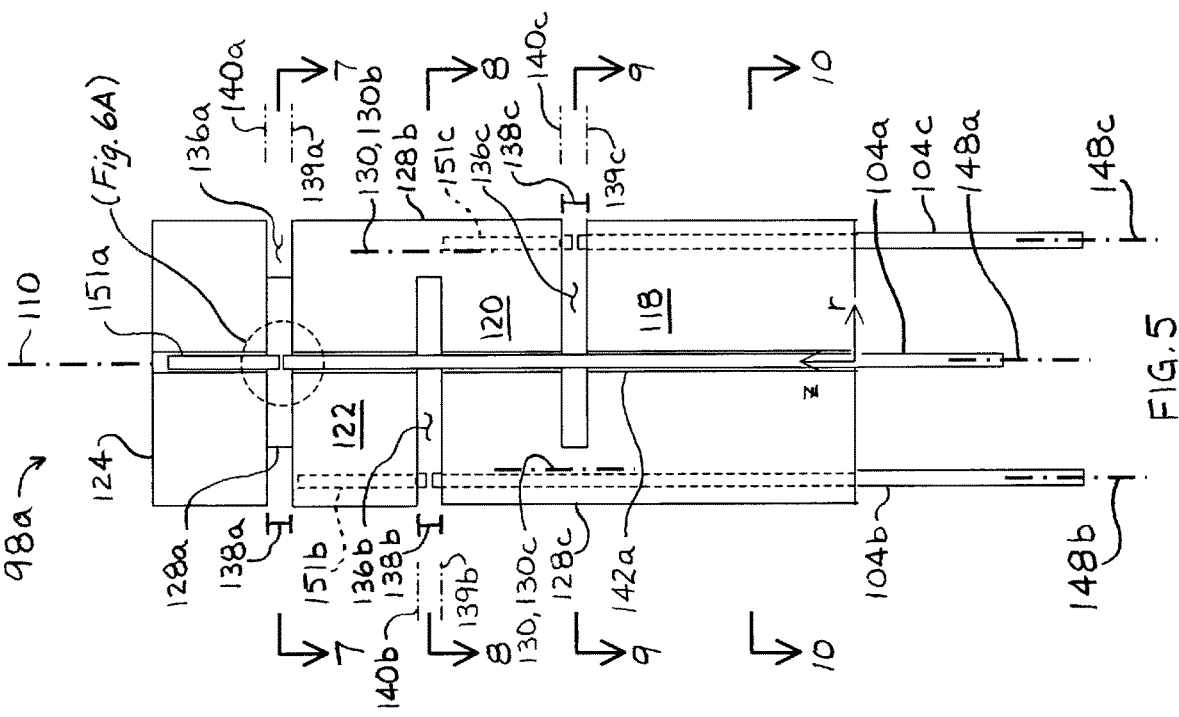
FIG. 5 is an elevation view of the fiber optic force sensing assembly of FIG. 4.

Referring to FIG. 3, an example of the end effector 88 comprising an ablation head 90 and including a fiber optic force sensing assembly 92 is depicted in an embodiment of the invention. The fiber optic force sensing assembly 92 can be configured as a multi-segmented structural member 96 that flexes in response to a contact force F imposed on a distal extremity 94 of the end effector 88, e.g., when distal extremity 94 contacts the wall of a bodily vessel or organ.

It is understood that one or more end effectors 58 of different kinds, e.g., mapping electrodes or ablation electrodes, such as are known in the art for diagnosis or treatment of a vessel or organ can be utilized with the invention. For example, the catheter assembly 57 can be configured as an electrophysiology catheter for performing cardiac mapping and ablation. In other embodiments, the catheter assembly 57 can be configured to deliver drugs or bioactive agents to a vessel or organ wall or to perform minimally invasive procedures such as transmyocardial revascularization or cryo-ablation.

Referring to FIGS. 4 through 11, a fiber optic force sensing assembly 98a including a four-segment structural member 102 and a plurality of fiber optics 104 is depicted in an embodiment of the invention. In this embodiment, the four-segment structural member 102 defines a longitudinal axis 110 and includes an outer surface 112. The four-segment structural member 102 is divided into four segments 116, identified as a proximal segment 118, a first middle segment 120, a second middle segment 122 and a distal segment 124. The segments 116 are sequentially adjacent each other in a serial arrangement along the longitudinal axis 110.

Figures 6A, 6B, 6C, 15:
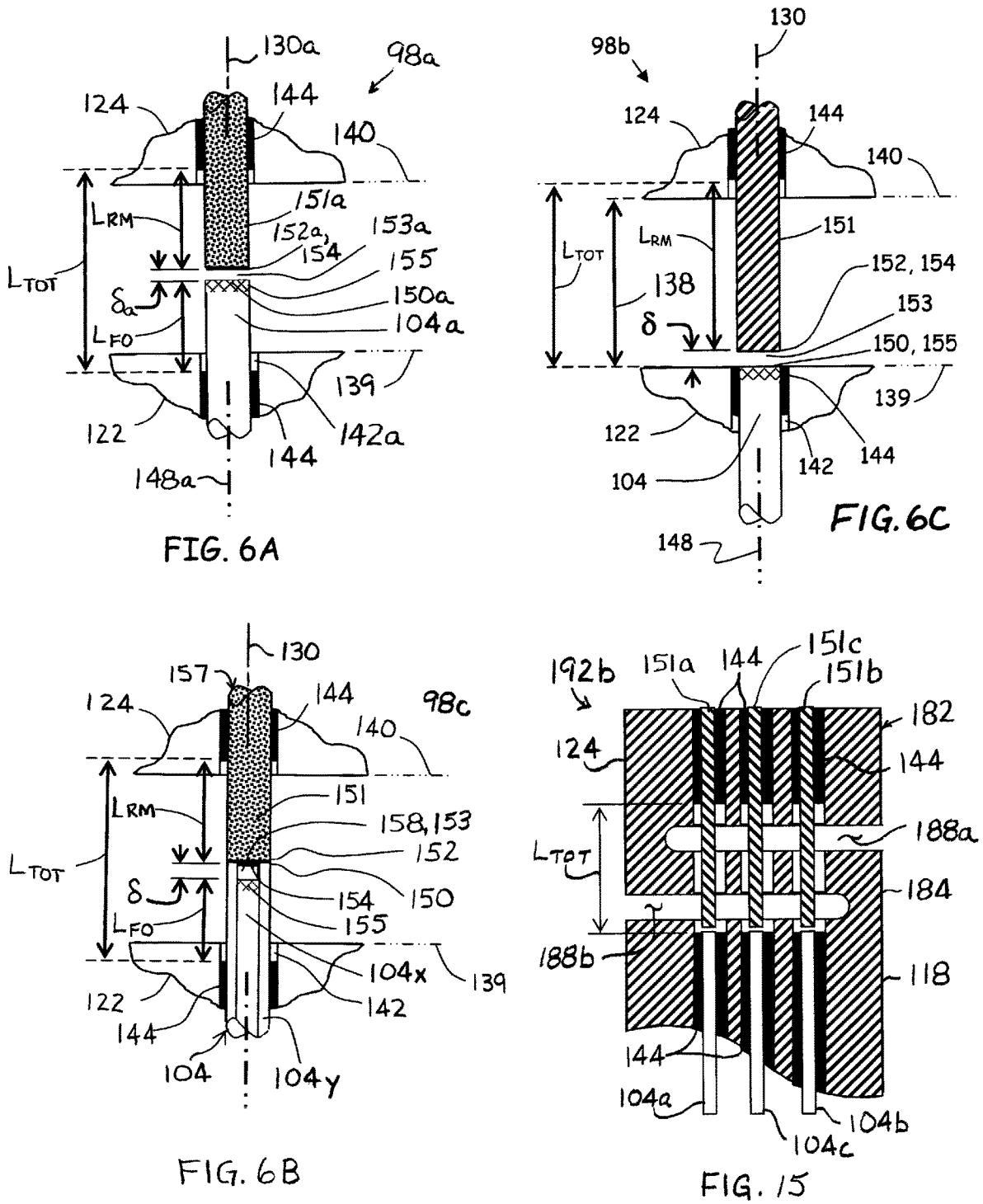
FIG. 6A is a partial enlarged view of an interferometric gap of the force sensing assembly of FIG. 5.
FIG. 6B is a partial enlarged view of an intrinsic interferometric gap of a fiber optic force sensing assembly in an embodiment of the invention.
FIG. 6C is a partial enlarged view of an interferometric gap of a force sensing assembly in an embodiment of the invention.
FIG. 15 is a sectional view of a fiber optic force sensing assembly in an embodiment of the invention.
Figures 7, 8, 9, 10, 11:
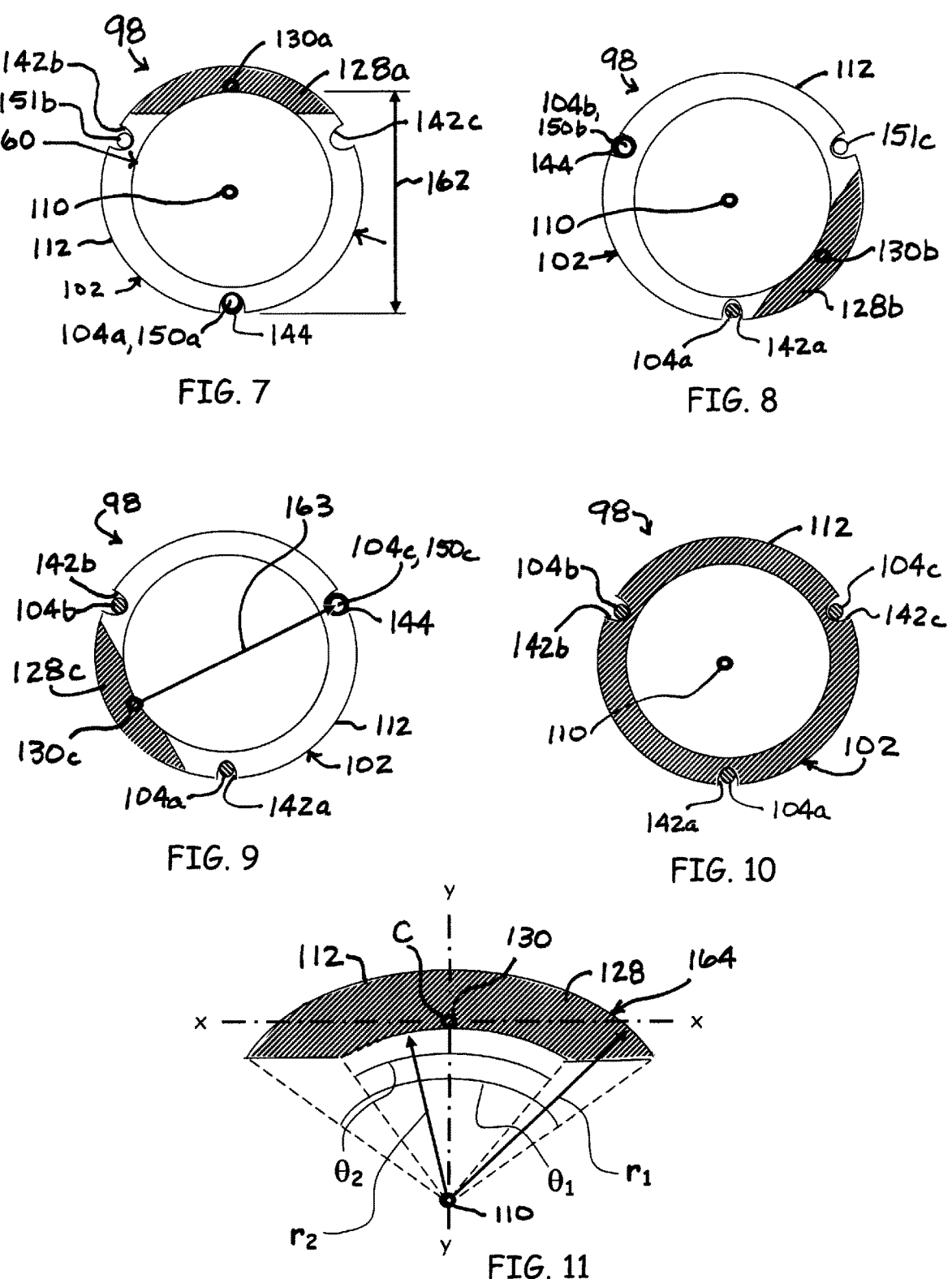
FIGS. 7 through 10 are sectional views of the fiber optic force sensing assembly of FIG. 5.
FIG. 11 is an enlarged sectional view of a flexure defining a circular segment in an embodiment of the invention.

In one embodiment, the segments 116 are bridged by a plurality of flexures 128, identified individually as flexures 128a, 128b and 128c, thus defining a plurality of flexural axes 130, identified individually as flexural axes 130a, 130b and 130c (best depicted in FIGS. 7, 8 and 9). In one embodiment, adjacent members of the segments 116 define a plurality of slots 136, each having a separation dimension 138 and each defining a proximal plane 139 and a distal plane 140 (FIG. 6A). For clarity, the slots 136 and separation dimensions 138 are identified as 136a through 136c and 138a through 138c, respectively. The separation dimensions 138a, 138b and 138c can be of the same approximate magnitude (as depicted) or of different magnitudes (not depicted). Each slot 136 defines its own proximal plane 139 and distal plane 140, depicted in FIG. 5 as 139a through 139c and 140a through 140c, respectively.

The four-segment structural member 102 can include a plurality of grooves 142 (identified as grooves 142a, 142b and 142c) formed on the outer surface 112. The grooves 142 can be spaced rotationally equidistant (e.g., spaced 120° apart for a 3-fiber system) about the longitudinal axis 110 and can be oriented in a substantially axial direction along the four-segment structural member 102.

The fiber optics 104 (identified as fiber optics 104a, 104b and 104c) define a plurality of light propagation axes 148 and distal ends 150 (identified as 148a through 148c and 150a through 150c, respectively). The fiber optics 104 are disposed in the grooves 142 and can be affixed thereto with a potting 144 such as epoxy such that the distal ends 150 terminate proximate the proximal planes 139 of the slots 136 (FIG. 6A). Alternatively or in addition to the potting 144, the fiber optics 104 can be press fit or otherwise fastened to the four-segment structural member 102. The fiber optic 104 can be bonded to the segment 116 adjacent the respective slot 136 to be interrogated. For example, fiber optic 104b can be mounted within the portion of groove 142b that is formed on the middle segment 122. The remainder of the fiber optic 104b can be left to slide freely within the remainder of the groove 142b, such that the fiber optic 104b will not form a structural bridge between adjacent segments, which would inhibit the flexibility of the fiber optic force sensing assembly 98a.

Referring again to FIG. 6A, the fiber optic 104a can extend along the groove 142a, terminating proximate the proximal plane 139 of the slot 136a. Likewise, fiber optics 104a and 104b can extend along the grooves 142b and 142c, respectively, terminating proximate the slots 136b and 136c, respectively. In one embodiment, reflecting members 151 (identified as reflecting members 151a, 151b and 151c) each having a proximal end 152 (identified as proximal ends 152a, 152b and 152c) are arranged so that the proximal ends 152 are proximate the distal plane 140 of a given slot 136. Each of the reflecting members 151 is paired and substantially aligned with the distal end 150 of a corresponding one of the plurality of fiber optics 104. A plurality of gaps 153 (identified as gaps 153a, 153b and 153c) are defined, one between each distal end 150 of the respective fiber optic 104 and the proximal end 152 of the reflecting member 151.

To be "proximate" a given plane 139 or 140 is defined for purposes of the claimed inventions as being closer to one of those planes than to the other, but not necessarily flush with the plane. For example, the distal end 150a is said to be "proximate" the proximal plane 139a if it is flush with, slightly recessed from or extends slightly beyond the proximal plane 139a (the latter being depicted in FIG. 6A) and closer to proximal plane 139a than to distal plane 140a. Likewise, the proximal end 152a of the reflecting member 151a is "proximate" the distal plane 140a if it is flush with, slightly distal to or extending slightly proximal to the distal plane 140a (again, the latter being depicted in FIG. 6A), and closer to distal plane 140a than to proximal plane 139a.

The gaps 153 can be, for example, interferometric or intensity-varying. An "interferometric gap" as used herein is a gap having the attributes an interferometric resonator, such as found in a Michelson interferometer or a Fabry-Perot resonator. Likewise, a "gap interferometer" as used herein is an interferometer that utilizes an interferometric gap to produce an interference pattern. An "intensity-varying gap" is one configured to capture a reflected intensity that varies inversely with the dimension of the gap.

The gaps 153 may be characterized as having a dimension or operative length δ (δa being depicted for gap 153a in FIG. 6A) defined as the distance between the distal end 150 of the fiber optic 104 and the respective proximal end 152 of the reflecting member 151. The operative length δ can differ from the dimension of the respective slot 136 and can be different for each slot 136. The operative length δ establishes the characteristics of the reflected radiation (i.e., the frequency of the interference pattern or the intensity of the reflected radiation) returned back through the fiber optic 104. The distal ends 150 can be faced with a semi-reflecting surface or coating 155 that re-reflects a portion of the light reflected from a highly reflective surface or coating 154 while substantially transmitting the remaining portion of the reflected light therethrough for detection by the displacement sensing system 40. In certain embodiments, the highly reflective surface 154 does not require a coating, but can be provided by the material of the reflecting member 151.

The fiber optic 104a of FIG. 6A is depicted as having a free length $L_{FO}$, defined as the distance between the distal end 150a and the potting 144 that affixes the fiber optic 104 to the groove 142a. Likewise, the reflecting member 151a is depicted as having a free length $L_{RM}$, defined as the distance between the proximal end 152a and the potting 144 that affixes the reflecting member 151a to the groove 142a. Herein, the distance between the pottings 144 is referred to as the total distance $L_{TOT}$. In some embodiments, the total distance $L_{TOT}$ between the pottings 144 will be substantially equal to the dimension of the slot 136. That is, the pottings 144 will be flush with the proximal and distal planes 139 and 140. The dimensions $L_{TOT}$, $L_{RM}$ and $L_{FO}$ can vary for each fiber optic/reflecting member pairing 104a/151a, 104b/151b and 104c/151c.

By the above described arrangement, each of the light propagation axes 148 of the fiber optics 104 is coincident with the proximal end 152 of the paired reflecting member 151. For example, as depicted in FIG. 6A, the light propagation axis 148a is subtended by the proximal end 152a of the reflecting member 151a. The proximal ends 152 of the reflecting members 151 can be made highly reflective. The distal ends 150 of the fiber optics 104, on the other hand, can be made only partially reflective to establish the Fabry-Perot effect. When electromagnetic radiation is transmitted through the fiber optics 104, the interaction between the highly reflective proximal ends 152 of the reflecting members 151 and the partially reflective distal ends of the fiber optics 104 creates interreflections therebetween, thus establishing an interference pattern having a frequency which depends on the dimension of the gap 153. The resulting modulated waveform 74a is transmitted back through the fiber optics 104 as explained in the discussions attendant FIGS. 1 and 2.

In another embodiment, the distal ends 150 of the fiber optics 104 are not treated with the semi-reflective coating, and in fact can be treated with an anti-reflective coating (not depicted). Such an arrangement can enhance or optimize the intensity of reflected radiation that is returned to the receiver 46 via the fiber optic 53 (FIG. 1). The size of the gap 153 can be inferred from intensity of the reflected light returned as detected by the receiver 46. The intensity of the reflected light collected by a given fiber optic 104 can vary with the distance between the distal end 150 and the reflective surface 154 proximal end 152 of the reflecting member 151.

Referring now to FIG. 6B, a fiber optic force sensing assembly 98c is portrayed as having a spliced fiber optic 157 with an intrinsic interferometric cavity 158 in an embodiment of the invention. The fiber optic force sensing assembly 98c includes many of the same aspects as the force sensing assembly 98a, which are identified by like-numbered numerical references. The depiction of FIG. 6B limns both the core 104x and the cladding 104y of the fiber optic 104.

The spliced fiber optic 157 includes the fiber optic 104 and the reflecting member 151, but instead of a gap being defined between non-touching ends, the intrinsic interferometric cavity 158 is captured between the distal end 150 of the fiber optic 104 and the proximal end 152 of the reflecting member 151 by splicing the ends 150 and 152 together. The gap 153 is thus defined between the axial ends of the cavity 158.

Prior to the splicing operation, the cavity 158 is formed on at least one of the ends 150 and/or 152. (The depiction of FIG. 6B is a non-limiting portrayal of the cavity formed on the distal end 150 of the fiber optic 104.) The cavity 158 can be formed, for example, by a chemical erosion or a laser ablation process that removes material from the core 104x and leaves effectively only the cladding 104y remaining. Thereafter, the highly reflective and partially reflective coatings 154 and 155, respectively, can be applied to the ends of the reflecting member 151 and the fiber optic 104, respectively, and the fiber optics 104 and the reflecting member 151 are spiced together.

The spliced fiber optic 157 or any other version of an intrinsic interferometric device will mechanically bridge the slots 136 at the location of the deflection beam length 163 of the respective slot. The mechanical bridging effectively increases the rigidity of the force sensing assembly 98c. To maintain a desired sensitivity to contact force, the bending resistance or "stiffness" of the opposing flexure 128 can be reduced in proportion to the increased rigidity caused by the presence of the bridging fiber optic. (See FIG. 11 and attendant discussion of area moments of inertia.) In the extreme, the elasticity of the assembly can be delegated to the bridging fiber optics by elimination of the flexures 128 (not depicted).

In various embodiments, the structural member is made of a metallic material, such as titanium, whereas the fiber optics are made of a material that is highly transparent at select wavelengths, such as silica or sapphire. The coefficient of thermal expansion (CTE) of these materials is substantially different, with silica being in the range of 1 to $2\times10^{-6}$ m/m-K (1 to 2 $\mu$/K), and titanium being more on the order of 8 $\mu$/K. The difference in the respective CTE can cause substantial thermally-induce changes in the operative lengths $\delta$ of the gaps 153 that, if uncorrected or uncompensated, can lead to large errors in the indications of contact force.

As alluded to previously, the segments 116 and flexures 128 of the metallic material will change in proportion to the CTE of the metallic material. Accordingly, the total distance between the pottings 144 of a given fiber optic 104 and its paired reflecting member 151 will change in proportion to the CTE of the metallic material and for a given temperature change. Meanwhile, the free lengths $L_{FO}$ and $L_{RM}$ will change in proportion to the CTEs of the reflecting member 151 and the fiber optic 104, respectively. Mathematically, this relationship is expressed as $$(1+\alpha_M \cdot \Delta T_M) \cdot L_{TPT} - (1+\alpha_{FO} \cdot \Delta T_{FO}) \cdot L_{FO} - (1+ \alpha_{RM} \cdot \Delta T_{RM}) \cdot L_{RM} = \delta \qquad \text{Eqn. (1)}$$

where $\alpha$ is the CTE, $\Delta T$ is the local change in temperature, $\delta$ is the operative length of the gap 153/cavity 158, and subscripts M, FO and RM designate the metal, fiber optic and reflecting member, respectively. The quantity $\alpha_M \cdot \Delta T_M \cdot L_{TOT}$ is the change in length between the pottings 144 that is attributed to temperature change of the metallic structural member, and the quantities $\alpha_{FO} \cdot \Delta T_{FO} \cdot L_{FO}$ and $\alpha_{RM} \cdot \Delta T_{RM} \cdot L_{RM}$ are the changes in length of the extended portions of the fiber optic 104 and the reflecting member 151 due to their respective temperature changes.

A further simplifying assumption is to assume $\Delta T_{FO}$ and $\Delta T_{RM}$ are dominated by and substantially equal to $\Delta T_M$ for the corresponding slot. That is, $\Delta T_{FO} = \Delta T_M = \Delta T_{RM} = \Delta T$. The change in $\delta$ due to the change in temperature then becomes $$\partial \delta / \partial T = \alpha_M \cdot L_{TOT} - \alpha_{FO} \cdot L_{FO} - \alpha_{RM} \cdot L_{RM} \qquad \text{Eqn. (2)}$$

Thus, for a given total temperature change $\Delta T$, a thermally-induced change in the gap dimension $\Delta \delta$ is approximated by $$\Delta \delta = (\alpha_M \cdot L_{TOT} - \alpha_{FO} \cdot L_{FO} - \alpha_{RM} \cdot L_{RM}) \cdot \Delta T \qquad \text{Eqn. (3)}$$

where $\Delta T$ is the change in temperature relative to a reference temperature. Knowing the various $\alpha$ and L values of Eqn. 3, one can actively compensate for the thermally-induced change in gap dimension $\Delta \delta$ by measuring the $\Delta T$.

Note that the quantity $(\alpha_M \cdot L_{TOT} - \alpha_{FO} \cdot L_{FO} - \alpha_{RM} \cdot L_{RM})$ can be reasonably approximated as a constant value across the temperature range of interest (e.g., from 0 to 40° C.). Thus, Eqn. (3) can be reduced to $$\Delta \delta = \Psi \cdot \Delta T \qquad \text{Eqn. (4)}$$

where $\Psi=(\alpha_M \cdot L_{TOT}-\alpha_{FO}\cdot L_{FO}-\alpha_{RM}\cdot L_{RM})$. In one embodiment, the value of $\Psi$ can be calibrated by measuring $\Delta\delta$ at different $\Delta T$. The value of $\Psi$ can be approximated as a constant, or taken as a temperature-dependent parameter by performing a curvefit to the calibration data.

The relationship of Eqn. (1) can also be utilized for establishing relationships for the passive correction of thermally-induced dimensional changes. At the reference temperature, $\Delta T_M$, $\Delta T_{FO}$ and $\Delta T_{RM}$ are all zero so that the length changes $\alpha_M \cdot \Delta T_M \cdot L_{TOT}$, $\alpha_{FO}\cdot\Delta T_{FO}\cdot L_{FO}$ and $\alpha_{RM}\cdot\Delta T_{RM}\cdot L_{RM}$ due to thermal expansion/contraction are all zero, and Eqn. (1) reduces to $$L_{TOT}-L_{FO}-L_{RM}=\delta \qquad \text{Eqn. (5)}$$

A simplifying assumption is to assume $\Delta T_{FO}$ and $\Delta T_{RM}$ are dominated by and equal to $\Delta T_M$. That is, $\Delta T_M=\Delta T_{FO}=\Delta T_{RM}=\Delta T$.

Mathematically, Eqns. (1) and (5) can be equated and the $\delta$ and $\Delta T$ parameters isolated and eliminated to give $$\alpha_M \cdot L_{TOT}-\alpha_{FO}\cdot L_{FO}-\alpha_{RM}\cdot L_{RM}=0 \qquad \text{Eqn. (6)}$$

Physical realization of Eqn. (6) is achieved by proper selection of the various parameters, thus holding the operative length $\delta$ constant across a range of temperature changes $\Delta T$. By assigning values to all but one of the parameters in Eqn. (6), the value of the remaining parameter can be established.

Equation (3) can be used generally for parametric studies for selecting proper free lengths for given combinations of CTEs available. In particular, the presence of the reflecting members 151 of the FIG. 6A and FIG. 6B configurations offers a way to passively compensate for thermally induced changes in the dimensions of the structural member 102 and the attendant changes in the operative length $\delta$. For example, if the CTEs $\alpha_M$, $\alpha_{FO}$ and $\alpha_{RM}$ are known, and the lengths $L_{TOT}$ and $L_{FO}$ are known or assigned values, the free length of the reflecting member $L_{RM}$ can be solved:

$$L_{RM}=(\alpha_M \cdot L_{TOT}-\alpha_{FO}\cdot L_{FO})/\alpha_{RM} \qquad \text{Eqn. (7)}$$

Alternatively, for example, if the CTEs $\alpha_M$ and $\alpha_{FO}$ are known, and the lengths $L_{TOT}$, $L_{FO}$ and $L_{RM}$ are assigned values, the required CTE of the reflecting member $\alpha_{RM}$ can be solved:

$$\alpha_{RM}=(\alpha_M \cdot L_{TOT}-\alpha_{FO}\cdot L_{FO})/L_{RM} \qquad \text{Eqn. (8)}$$

Referring to FIG. 6C, a fiber optic force sensing assembly 98b is depicted in an embodiment of the invention. In this embodiment, the fiber optic 104 is mounted substantially flush with the proximal plane 139 of the slot 136, and the reflecting member 151 is arranged to extend substantially the length $L_{TOT}$ except for the allowance for the operative length $\delta$. Also in the FIG. 6C embodiment, the reflecting member 151 is made of the same material as the structural member 102, or at least of a material that has the same CTE as the reflecting member 151. In one embodiment, the structural member 102 is fabricated from titanium, and the reflecting members 151 comprise titanium rods or wires that are affixed to the structural member 102 with the potting 144 (as depicted) or by a welding process. In another embodiment (not depicted), the reflecting members 151 are integrally formed with the structural member 102.

Functionally, for the configuration of sensing assembly 98b, matching the CTE of the structural member 102 and the reflecting member 105 substantially compensates for temperature changes of these components. Generally, because the length $L_{RM}$ is only slightly less than the separation dimension 138, the change in the length $L_{RM}$ of the reflecting member 151 is close to the change in the separation dimension 138. In this way, the change in the separation dimension 138 is largely offset by the change in the reflecting member 151.

A simplification results when the fiber optic 104 does not extend beyond the potting 144, such as the presented in the configuration of FIG. 6C. Consider the scenario where the sensing assembly 98b undergoes an increase in temperature. This will cause the separation dimensions 138 of the slots 136 to increase, thereby causing the distance $L_{TOT}$ to increase also. But the reflecting member 151, being of the same CTE and almost of the same length, will increase in length by almost the same length, causing the reflecting member 151 to grow towards the distal end 150 of the fiber optic 104 at the same time that the increase in the separation dimension brings the distal end 150 of the fiber optic towards the proximal end 152 of the reflecting member 151.

The same mechanism of compensation occurs when the sensing assembly 98b decreases in temperature. The separation dimensions 138 decrease, and so does the length $L_{RM}$ of the reflecting member 151, causing the reflecting member to shrink away from the distal end 150 of the fiber optic 104 just as the decrease in the separation dimension brings the distal end 150 of the fiber optic towards the proximal end 152 of the reflecting member 151.

In mathematical terms, the simplification is rooted in the reduction of the free length $L_{FO}$ of the fiber optic 104 to zero. For $L_{FO}=0$, Eqn. (1) reduces to $$(1+\alpha_M \cdot\Delta T_M)\cdot L_{TOT}-(1+\alpha_{RM}\cdot\Delta T_{RM})\cdot L_{RM}=\delta \qquad \text{Eqn. (9)}$$

Assuming $\Delta T_M=\Delta T_{RM}=\Delta T$, and noting that a change in the temperature $\partial T$ is the same as a change in the $\partial\Delta T$, a change in the gap dimension $\partial\delta$ due to the change in temperature $\partial T$ is expressed as $$\partial\delta/\partial T=\alpha_M \cdot L_{TOT}-\alpha_{RM}\cdot L_{RM} \qquad \text{Eqn. (10)}$$

For systems where the reflective members 151 have the same CTE as the structural member (i.e., $\alpha_{RM}=\alpha_M$), Eqn. (10) further simplifies to $$\partial\delta/\partial T=\alpha_M \cdot(L_{TOT}-L_{RM})=\alpha_M \cdot\delta \qquad \text{Eqn. (11)}$$

For a given total temperature change $\Delta T$, a change in the gap dimension $\Delta\delta$ is approximated by $$\Delta\delta=\alpha_M \cdot\delta\cdot\Delta T \qquad \text{Eqn. (12)}$$

It is noted that Eqn. (12) applies regardless of the lengths $L_{TOT}$ or $L_{RM}$.

The change in the length between the pottings 144 due to thermal effects, expressed in Eqn. (1) as $\alpha_M \cdot\Delta T_M \cdot L_{TOT}$, is proportional to the dimension $L_{TOT}$ between pottings 144. That is, the greater the value of $L_{TOT}$, the greater the potential error due to thermal changes. Therefore, the value of $L_{TOT}$ can be substantially greater for the fiber optic force sensing assembly 192a than for the assembly 180.

For example, in a representative and non-limiting embodiment, the operative length $\delta$ is approximately 15 µm, with force sensitivity in the range of 0.1 to 0.25 grams of force (gmf) per nanometer (nm) of axial displacement (i.e., a displacement sensitivity ranging from 4 to 10 nm/gmf), where a "gram of force" is equivalent to the weight of 1 gram of mass at standard gravity. The CTE of titanium is approximately 8 µ/K. Representative (i.e., non-limiting) values for $L_{TOT}$ range from approximately 0.2 mm to 1 mm. Using these representative and non-limiting values, the sensitivity to temperature change ranges from 0.4 to 1 gmf/K. In many applications, it is desirable to resolve the force to within ±1 gmf. Thus, desired resolution of the force sensing system can become dwarfed by the thermally-induced error in uncompensated systems where temperature changes several Kelvins during ablation operations.

However, countering the effects of temperature change can be accomplished using the aspects and methods described above. The reflecting members 151, having highly reflective proximal ends 152, are not relied upon to transmit light. Thus, the CTE of the reflecting members 151 can be tailored for a desired CTE without consideration of the light transmittance properties. Therefore, in one embodiment, the reflecting members 151 can be replaced with fibers having a high CTE, provided, for example, by aluminum doped fibers having a CTE of around 4 μ/K. In another embodiment fibers of sapphire with CTE of 12 μ/K can be employed. Fine tuning of the passive compensation can be obtained by changing the relative length of the sapphire normal fiber in accordance with Eqn. (6).

For the configuration of FIG. 6C, consider again the example of the structural member 102 being made of titanium having a CTE ($\alpha_M$) of 8 μ/K and having an operative length δ of 15 μm. The resulting change in the gap dimension Δδ in accordance with Eqn. (11) would be 0.120 nm per K. In a system having a force sensitivity of approximately 4 nm/gmf, the resulting error would be on the order of 0.015 gmf/K—an improvement of almost two orders of magnitude over an uncompensated system.

Accordingly, where $L_{FO}$ is reduced to zero, selecting a CTE for the reflective members 151 that is the same as the CTE of the structural member largely cancels the effects of thermal expansion or contraction. In some embodiments, the material of the reflecting member 105 can have sufficient reflectance to negate the need for a coating. Proximal ends 152 can be polished to provide the totally reflective surface, and/or can still be coated with a coating.

It is noted that the above-expressed Eqns. (1) through (12) apply to open gaps as well as for gaps defined by intrinsic interferometric cavities 158. The effect of the bridging caused by the spliced fiber optics 157 of FIG. 6B are readily calibrated out.

Figure 4:
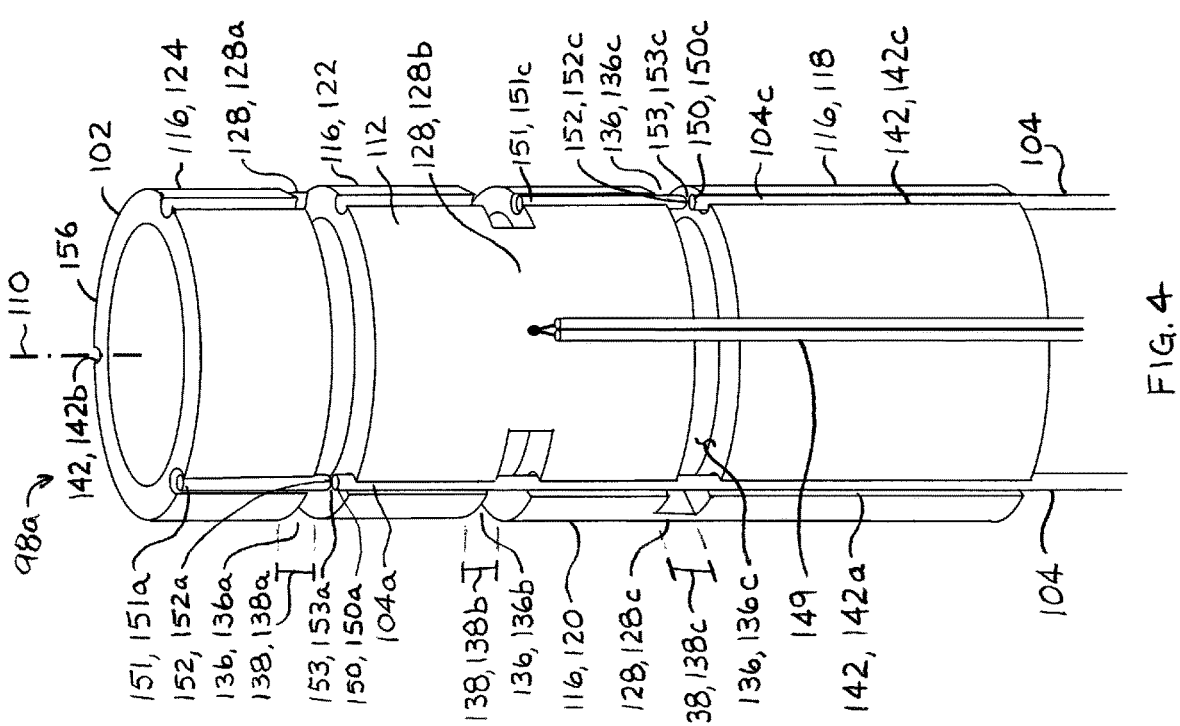
FIG. 4 is an enlarged perspective view of a fiber optic force sensing assembly in an embodiment of the invention.

In certain embodiments, each of the flexure portions 128 can be instrumented with temperature sensors for active compensation of temperature change. The depiction of FIG. 4 presents a thermocouple 149 that is routed along the exterior of the structural member 102 and arranged so that the temperature sensing junction of the thermocouple 149 is in contact with the outside surface of flexure portion 128b. In other embodiments, the temperature sensor can be routed along the interior of the structural member 102 and placed in sensing contact with the interior surfaces of the flexure portions.

In one embodiment, each of the flexure portions 128a, 128b and 128c are instrumented with a respective temperature sensor (not depicted). By sensing the temperature change of each flexure 128, the thermally-induced changes to the dimensions 138 can be inferred. The temperature sensors can be taken as the ΔT to solve for the change in the gap dimension Δδ (e.g., used to solve Eqns. (3), (4) or (12)) for active compensation.

In another embodiment, the values provided by the temperature sensors can be utilized in a calibration arrangement such as described in Leo '092, where the change in temperature of the local flexure $\Delta T_M$ is taken as the change in temperature of the displacement sensor. It is noted that, unlike the teachings of Leo '092, the temperature sensors 149 are not necessarily proximate the fiber optics 104 or reflecting members 151, but instead can actually be diametrically opposed to the fiber optic/reflecting member pairing that is being corrected by the temperature sensor 149.

In one embodiment of the invention, a method for actively compensating for thermally induced errors can be programmed into the computer-readable storage device 49 (FIG. 1). The computer-readable storage device 49 can be programmed to receive information from the temperature sensing module 66 based on signals received from the temperature sensor 62. A reference measurement can be made, for example, at room temperature with the force sensing assembly in a no-load condition. A temperature change of the force sensing assembly relative to the reference temperature can be measured, for example, at a flexure 128 of structural member 102. The computer-readable storage device 49 can be programmed to compute the change in the gap dimension due to the temperature change using, for example, the relationship expressed in Eqns. (3), (4) or (12).

The slots 136 can be formed so that they extend laterally through a major portion of the four-segment structural member 102. Also, the slots 136 can be oriented to extend substantially normal to the longitudinal axis 110 (as depicted) or at an acute angle with respect to the longitudinal axis (not depicted). In the depicted embodiment, the structural member comprises a hollow cylindrical tube 156 with the slots 136 being formed from one side of the hollow cylindrical tube 156, extending therethrough and across the inner diameter 160 of the hollow cylindrical tube 156 to a depth 162 (FIG. 7).

Referring again to FIGS. 7-11, cross-sections of the structural member 102 are depicted in an embodiment of the invention. The flexure portions 128 remaining after the slots 136 are formed, substantially define, for example, a major circular segment with a minor circular segment cut out (e.g., FIGS. 7-9 and 11). Alternatively, a circular segment with no cut out can also be defined (e.g., FIG. 14B). The depth 162 of the slots 136 traverse the inner diameter 160 of the hollow cylindrical tube 156 can be varied to establish a desired flexibility of the flexure 128. That is, the greater the depth 162 of the slot 136, the more flexible the flexure portion 128. The slots 136 can be formed by the various techniques and methods available to the artisan, such as but not limited to sawing, laser cutting or electro-discharge machining (EDM).

The slots 136 can be formed so that the flexure portions 128 define non-concentric flexural axes 130. By "non-concentric" flexural axes, it is meant that the respective flexural axes are not in axial alignment. That is, flexural axis 130a defines an axis in space that is non-coincident with either flexural axes 130b and 130c, and flexural axis 130b defines and axis in space that is non-coincident with flexural axis 130c. In certain embodiments, the flexural axes 130 are diametrically opposed to the location of the distal end 150 of the fiber optic 104 that terminates in the same slot 136 as is bridged by the flexural axis. For example, flexure portion 128a can be diametrically opposed to distal end 150a, and so on.

A cross-section 164 of the flexure portion 128 is depicted in FIG. 11. The cross-section is characterized by an area centroid C through which the neutral or flexural axis 130 passes, and as having inertial axes x-x and y-y that are orthogonal, where the inertial axis x-x identifies the axis about which the area moment of inertia is minimum. In some embodiments, the y-y axis passes substantially through the longitudinal axis 110. The circular segment geometry provides substantially greater stiffness about inertial axis y-y than about inertial axis x-x. Consider a circular segment having an angle of π/2 radians (90°). The area moment of inertia about the inertial axis y-y is about twenty times greater than the area moment of inertia about the inertial axis x-x. Accordingly, forces that cause a moment about inertial axis y-y will typically cause substantially less bending relative to the same moment being applied about inertial axis x-x. Therefore, moments about inertial axis y-y tend to be transferred as a torsional force between adjacent sections, whereas moments about inertial axis x-x will tend to cause a deformation of the flexure portion 128 and a subsequent deflection between the adjacent segments 116.

Figures 14, 14A, 14B:
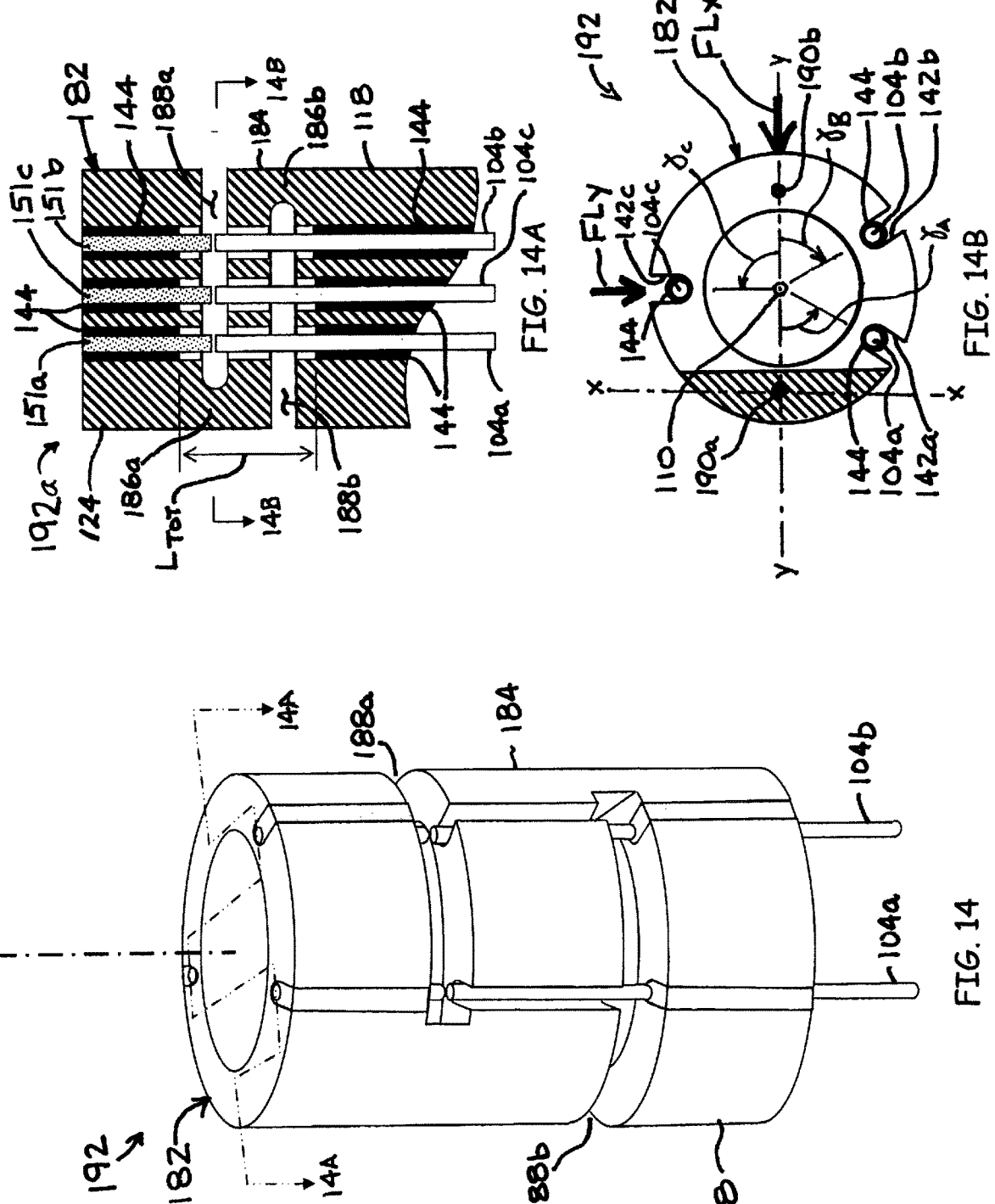
FIG. 14 is an enlarged perspective view of a fiber optic force sensing assembly in a third embodiment of the invention.
FIGS. 14A and 14B are sectional views of the force sensing assembly of FIG. 14.

A deflection beam length 163, depicted in FIGS. 9 and 14B, is defined as the distance between the flexural axis 130 and the propagation axis 148 at the distal end 150 of the corresponding fiber optic 104, the distance being normal to the inertial axis x-x. By locating, for example, the distal end 150c and the flexural axis 130c of the slot 136c in diametric opposition, the deflection beam length 163 is maximized, and so is the attendant change in the operative length δ of the gap 153 between the distal end 150 of the fiber optic 104 and the proximal end 152 of the reflecting member 151.

Referring to FIGS. 12A and 12B, operation of the fiber optic force sensing assembly 98a in response to an axial force FA and a lateral force FL, respectively, is depicted in an embodiment of the invention. The axial force FA causes the segments 116 to bend about the inertial axes x-x of the various flexure portions 128 in substantially a pure bending action, thus causing the dimension of the slots 136 proximate the distal ends 150 of the fiber optics 104 to decrease (FIG. 12A). This, in turn, causes the operative lengths δ of the gaps 153 to decrease, thereby causing a change in the characteristics of the reflected radiation received by the fiber optics 104 (i.e., the frequencies of the interferometric patterns sustained across the gaps 153, or the intensity of the reflected radiation).

The lateral force FL will generally cause a more complex deformation of the four-segment structural member 102. In the depiction of FIG. 10B, the lateral force FL is applied substantially parallel to the inertial axis y-y of flexure portion 128a. This causes flexure portion 128a to translate a moment between the distal segment 124 and the second middle segment 122 while causing a negligible change in the dimension δa of gap 153a. The translated moment causes flexure portions 128b and 128c to bend about their respective inertial axes x-x, which in turn causes the slot 136b to close proximate distal end 150b of fiber optic 104b and the slot 136c to open proximate the distal end 150c of fiber optic 104c. It is noted that in the depiction of FIG. 12B, neither flexure portion 128b or 128c are in pure bending because lateral force FL does not act normal to the respective inertial axes x-x. Hence, the degree of bending about the inertial axes x-x will generally be proportional to the component of the lateral force FL that acts normal thereto.

It is understood that FIGS. 12A and 12B show a purely axial and a purely lateral force, respectively, but that a combined force vector in three-dimensional space having an axial and a lateral component will combine the general effects depicted by superposition. Accordingly, a force vector in three-dimensional space can be resolved by calibrating the response of the fiber optic force sensing assembly under these pure loads and superimposing the various responses to infer the axial and lateral components.

The preceding embodiments can provide a mechanical amplification of the change in the operative length δ relative to the strain experienced by the flexure portions 128. The deflection of the segments 116 at a position normal to the inertial axis x-x of a respective one of the flexure portions 128 is proportional to the deflection beam length 163 between the inertial axis x-x and the respective location of the distal end 150 of the respective fiber optic 104. Accordingly, change in the dimension 138 of the slot 136 will be greatest at a location that is diametrically opposed to the flexural axis 130. Thus, for embodiments where the distal ends 150 of the fiber optics 104 in diametric opposition to the flexural axes 130 (as depicted in FIG. 9), the fiber optics 104 are in a position of greatest sensitivity.

The structural member 102 can be fabricated from other forms besides a hollow cylindrical tube, including but not limited to tubes or rods that define a square, rectangular or cross-shaped cross-section. The structural member 102 can comprise a metallic material, such as titanium or platinum/iridium, or a non-metallic material such as a polymer or ceramic.

The potting 144 can comprise a glue or epoxy and can be selected to closely match the coefficient of thermal expansion (CTE) of the structural member 102 and/or fiber optics 104, or to provide a CTE that is between the CTEs of the structural member 102 and fiber optics 104 to provide a transition therebetween. The potting 144 can also be chosen for flexibility so that the thermal growth of the adhesive film does not impose a substantial strain on the fiber optics 104. Use of a very thin film of potting 144 can, in some instances, mitigate the strain-inducing effects of differential thermal expansion between the fiber optic 104 and the structural member 102.

Referring to FIGS. 13, 13A and 13B, a fiber optic force sensing assembly 180 having a three-segment structural member 182 is depicted in an embodiment of the invention. The fiber optic force sensing assembly 180 includes many of the same aspects as the assembly 98a, which are identified by like-numbered numerical references. A distinction between the three-segment structural member 182 and the four-segment structural member 102 is that the three-segment structural member 182 includes only a single middle segment 184 between the proximal and distal segments 118 and 124. Also, the three-segment structural member is characterized by two flexures 186a and 186b that separate the middle segment 184 from the proximal and distal segments 118 and 124, respectively, thereby defining a distal or "distal-most" slot 188a and a proximal slot 188b, respectively.

The arrangement between the fiber optics 104 and reflecting members 151 can be the same as the various configurations described and discussed in relation to FIG. 6. The reflecting members can be configured for passive compensation of thermal expansion/contraction, or instrumented with temperature sensors for active compensation. Both passive and active compensation are described above.

In the depicted embodiment, the flexures 186a and 186b define respective flexural axes 190a and 190b that are rotationally spaced 180° apart (i.e., are diametrically opposed) so that the flexural axes 190a and 190b and the longitudinal axis 110 are substantially co-planar. Also by this arrangement, the inertial axes y-y of the flexures 186a and 186b are substantially coplanar. The fiber optics 104a and 104c and the corresponding reflecting members 151a and 151c of the fiber optic force sensing assembly 180 extend into the same distal slot 188a, and are spaced at an angle γ rotationally equidistant from the inertial axes y-y but respectively in opposite directions +γ and −γ.

In operation, the three-segment structural member 182 will respond to axial and lateral force components FA and FL in generally the same manner similar as that depicted in FIGS. 12A and 12B. Consider also the specific response to lateral force components FLx and FLy, depicted in FIG.

13B, where FLx is a lateral force component acting normal to inertial axis x-x and FLy is a lateral force component acting normal to inertial axis y-y. The lateral force component FLx will cause pure bending about the inertial axes x-x, causing dimensional changes in the distal and proximal slots 188a and 188b akin to the changes in dimensions 138c and 138b in slots 136c and 136b, respectively, that is depicted in FIG. 12B. The operative lengths δ of the various gaps 153 change in congruence with the dimensional changes of the distal and proximal slots 188a and 188b.

Detection of the lateral force component FLy, however, relies on deflection about the inertial axis y-y of the flexure 186a, which is sensed by changes in the operative lengths δ of the gap 153a and 153c. Because the stiffness of the flexures 186 about the y-y inertial axes is substantially greater than the stiffness about the x-x inertial axes, the sensitivity (measured displacement per unit force) to FLy force components is not as high as for FLx force components.

Referring to FIGS. 14, 14A and 14B, a fiber optic force sensing assembly 192a utilizing the three-segment structural member 182 is depicted in an embodiment of the invention. The fiber optic force sensing assembly 192a includes many of the same aspects as the assembly 180, which are identified by like-numbered numerical references. A distinction between the assemblies 180 and 192a is that, for the fiber optic force sensing assembly 192a, all of the fiber optics 104 are anchored to the proximal segment 118, pass through the proximal slot 188b and the single middle segment 184, and terminate proximate the distal slot 188a. Another distinction of the fiber optic force sensing assembly 192a is that the angular distribution of the optical fibers 104 and paired reflecting members 151 is not uniform, and that the fiber optics 104/reflecting members 151 are positioned for greater distances from the y-y inertial axes than with the fiber optic force sensing assembly 180 of FIG. 13. Accordingly, the rotational displacements γ relative to the y-y inertial axis are not all equal, but rather can be characterized by unique values γA, γB and γC. In the depicted embodiment, γA and γB are substantially equal.

The arrangement of the fiber optic force sensing assembly 192a depicted in FIG. 14 is more sensitive to lateral force components FLy than is the assembly 180 for several reasons. First, the displacement sensed is the accumulation of the displacements about both the flexures 186a and 186b. Second, the distance between the slots 188a and 188b afforded by the middle segment 184 provides a mechanical amplification of the flexural displacement about inertial axis y-y of the flexure 186b. Third, the rotational displacements γ of the fiber optic 104 and reflecting member 151 pairings relative to the plane of the y-y inertial axes are either at 90° (γC) or closer to 90° (γA, γB) than would be in a uniform angular distribution where the three fiber optics 104 are spaced 120° apart.

By increasing the angular displacement γA and γB relative to a uniform distribution, the sensitivity of the corresponding gaps 153a and 153b to the FLy component is increased with γ=90° providing the greatest sensitivity to the FLy component. It is also noted that the sensitivity to the FLx component is decreased as γ is increased. Here, the enhancements to the sensitivity of the FLy component are accomplished in part by a beneficial tradeoff with the sensitivity to the FLx components.

Therefore, the sensitivity to lateral forces of the fiber optic force sensing assembly 192a depicted in FIG. 14 is more uniform (less directionally dependent) than is the fiber optic force sensing assembly 180 of FIG. 13. The same passive compensation of changes due to temperature change can be implemented in both the FIG. 13 and the FIG. 14 configurations as discussed attendant to FIGS. 6A and 6B above. Active compensation for the fiber optic force sensing assemblies 180 or 192a of FIGS. 13 and 14 can also be enabled by instrumenting flexures 186a and 186b with temperature sensors.

Referring to FIG. 15, a fiber optic force sensing assembly 192b is depicted in an embodiment of the invention. The fiber optic force sensing assembly 192b has many of the same aspects as the fiber optic force sensing assembly 192a. A primary difference between assemblies 192a and 192b are that the reflecting members 151 extend through the distal slot 188a and are optically coupled with the fiber optics 104 near the proximal slot 188b. In the depicted embodiment, the reflecting members 151 are also made of the same material as the three-segment structural member 182. Alternatively, the reflecting members 151 are of a different material, but have the same CTE as the three-segment structural member 182.

Functionally, the fiber optic force sensing assembly 192b offers the same force sensitivity advantages as fiber optic force sensing assembly 192a. However, because the fiber optics 104 do not extend substantially beyond the potting 144, the same benefits explained above in relation to FIG. 6C are realized. See Eqns. (9)-(12) and attendant discussion.

The following references, included above, are hereby incorporated by reference in their entirety except for explicit definitions contained therein: International Publication Nos. WO 2007/015139 to Leo et al., WO 2010/079418 to Leo et al., WO 2009/114955 to Kistler et al.; U.S. Pat. No. 8,157,789 to Leo et al., U.S. Pat. No. 8,075,498 to Leo et al., U.S. Pat. No. 8,048,063 to Aeby et al.; United States Patent Application Publication No. 2009/0287092 to Leo et al.

References to relative terms such as upper and lower, front and back, left and right, or the like, are intended for convenience of description and are not contemplated to limit the invention, or its components, to any specific orientation. All dimensions depicted in the figures may vary with a potential design and the intended use of a specific embodiment of this invention without departing from the scope thereof.

Each of the additional figures and methods disclosed herein can be used separately, or in conjunction with other features and methods, to provide improved devices, systems and methods for making and using the same. Therefore, combinations of features and methods disclosed herein may not be necessary to practice the invention in its broadest sense and are instead disclosed merely to particularly describe representative embodiments of the invention.

For purposes of interpreting the claims for the present invention, it is expressly intended that the provisions of Section 112, sixth paragraph of 35 U.S.C. are not to be invoked unless the specific terms "means for" or "step for" are recited in the subject claim.

The invention claimed is:

1. A force sensor for use at a distal tip of a catheter, comprising:
    a structural member that defines a longitudinal axis and includes a plurality of segments defining one or more slots therebetween;
    a plurality of fiber optics operatively coupled with the structural member, each of the plurality of fiber optics having a distal end that is proximate a corresponding reflecting member to define a respective gap therebetween, each of the plurality of fiber optics being oriented to emit light across the respective gap and onto the corresponding reflecting member, wherein the structural member is configured to produce a change in a dimension of at least one of the respective gaps in response to a force exerted on the distal tip of the catheter;

wherein a rotational displacement of each of the plurality of fiber optics and the corresponding reflecting members relative to a plane of y-y inertial axes is between about 60° and about 90°; and wherein a sensitivity of each of the respective gaps is optimized with respect to lateral force components.

2. The force sensor of claim 1, wherein the distal ends of the plurality of fiber optics are adapted for collection of at least a portion of the light reflected from the corresponding reflecting member.

3. The force sensor of claim 1, wherein the structural member further comprises:

a first segment and a second segment that are adjacent each other along the longitudinal axis, the first segment and the second segment defining a first slot therebetween, the first slot being bridged by a first flexure, and a third segment adjacent the second segment along the longitudinal axis, the second and third segments defining a second slot therebetween, the second slot being bridged by a second flexure.

4. The force sensor of claim 3, wherein the first flexure is centered about a first flexural axis that is parallel to the longitudinal axis, the second flexure is centered about a second flexural axis that is parallel to the longitudinal axis, and wherein the first flexural axis, the second flexural axis, and the longitudinal axis are substantially coplanar.

5. The force sensor of claim 3, further comprising at least two temperature sensors, each configured to detect a temperature of the structural member, a first of the at least two temperature sensors being centered substantially at an interface of the first flexure and the second segment, and a second of the at least two temperature sensors being centered substantially at an interface of the second flexure and the second segment.

6. The force sensor of claim 3, wherein the rotational displacement of the plurality of fiber optics and the corresponding reflecting members is such that each of the plurality of fiber optics and the corresponding reflecting members is either at or close to 90° relative to a plane of inertial axes of the first flexure and the second flexure.

7. The force sensor of claim 1, wherein each of the respective gaps is a Fabry-Perot resonator.

8. The force sensor of claim 1, wherein the force sensor is configured to passively compensating for changes in the dimensions of the respective gaps that are caused by temperature changes.

9. The force sensor of claim 1, wherein the corresponding reflecting members comprise a material having a coefficient of thermal expansion that differs from the plurality of fiber optics.

10. The force sensor of claim 1, wherein a material of the corresponding reflecting members is one of metallic doped fiber optic and a sapphire fiber.

11. A force sensor for use at a distal tip of a catheter, comprising:

a structural member;

a plurality of reflecting members, each affixed to and extending from the structural member; and a plurality of fiber optics, each paired with a corresponding one of the plurality of reflecting members, each paired fiber optic and reflecting member defining a corresponding gap therebetween, wherein the plurality of reflecting members each comprises a material having a coefficient of thermal expansion differing from that of the plurality of fiber optics, the coefficient of thermal expansion of the reflecting member being selected for passive compensation of changes in the corresponding gaps between each paired fiber optic and reflecting member that are caused by temperature change, wherein the structural member is configured to produce a change in a dimension of at least one of the corresponding gaps in response to a force exerted on the distal tip of the catheter, wherein a rotational displacement of each of the plurality of fiber optics and the corresponding reflecting members relative to a plane of y-y inertial axes is between about 60° and about 90°, and wherein a sensitivity of each of the corresponding gaps is optimized with respect to lateral force components.

12. The force sensor of claim 11, wherein the coefficient of thermal expansion of the reflecting members is different from that of the structural member.

13. The force sensor of claim 11, wherein the structural member includes a plurality of segments that define a plurality of slots, and a plurality of the corresponding gaps defined by the paired fiber optics and reflecting members are located within a common one of the plurality of slots.

14. The force sensor of claim 11, wherein the structural member includes an outer surface and a plurality of flexures, and wherein each of the flexures defines a portion of the outer surface of the structural member.

15. The force sensor of claim 11, wherein at least one of the fiber optics is a spliced with the respective reflecting member, the gap being defined by a cavity defined between the fiber optic and the respective reflecting member.

16. The force sensor of claim 11, wherein the structural member includes a plurality of segments that define a plurality of slots, proximal ends of the plurality of reflecting members are all proximate one of the plurality of slots, the one of the plurality of slots being the distal-most or the proximal-most of the plurality of slots.

17. The force sensor of claim 11, wherein the plurality of reflecting members and the structural member have the same coefficient of thermal expansion.

18. The force sensor of claim 11, wherein the structural member comprises a plurality of segments defining a plurality of slots, the plurality of fiber optics are affixed to a proximal-most of the plurality of segments and extend so that the corresponding gaps of the paired fiber optics and the reflecting members are proximate the proximal-most of the plurality of slots.

19. A force sensor for use at a distal tip of a catheter, comprising:

a structural member that defines a longitudinal axis and includes a first segment and a second segment that are adjacent each other along the longitudinal axis, the first and second segments defining a first slot therebetween, the first slot being bridged by a first flexure, and a third segment adjacent the second segment along the longitudinal axis, the second and third segments defining a second slot therebetween, the second slot being bridged by a second flexure;

a plurality of reflecting members, each affixed to and extending from the third segment of the structural member and each including a reflective surface; and a plurality of fiber optics, each paired with a corresponding one of the plurality of reflecting members and each oriented and adapted to irradiate the reflective surface of the corresponding one of the plurality of reflecting members and to collect at least a portion of a light reflected from a proximal end of a corresponding reflecting member, each paired fiber optic and reflecting member defining a corresponding gap having a dimension there between, each of the corresponding gaps being disposed proximate the second slot, wherein the force sensor is configured to compensate for thermally induced changes to each of the dimensions of the corresponding gaps, wherein a rotational displacement of each of the plurality of fiber optics and the corresponding reflecting members relative to a plane of y-y inertial axes is between about 60° and about 90°, and wherein a sensitivity of each of the respective gaps is optimized with respect to lateral force components.

20. The force sensor of claim 19, wherein the force sensor is configured to passively compensate for thermally induced changes to each of the dimensions of the corresponding gaps.

* * * * *